Figure 1:
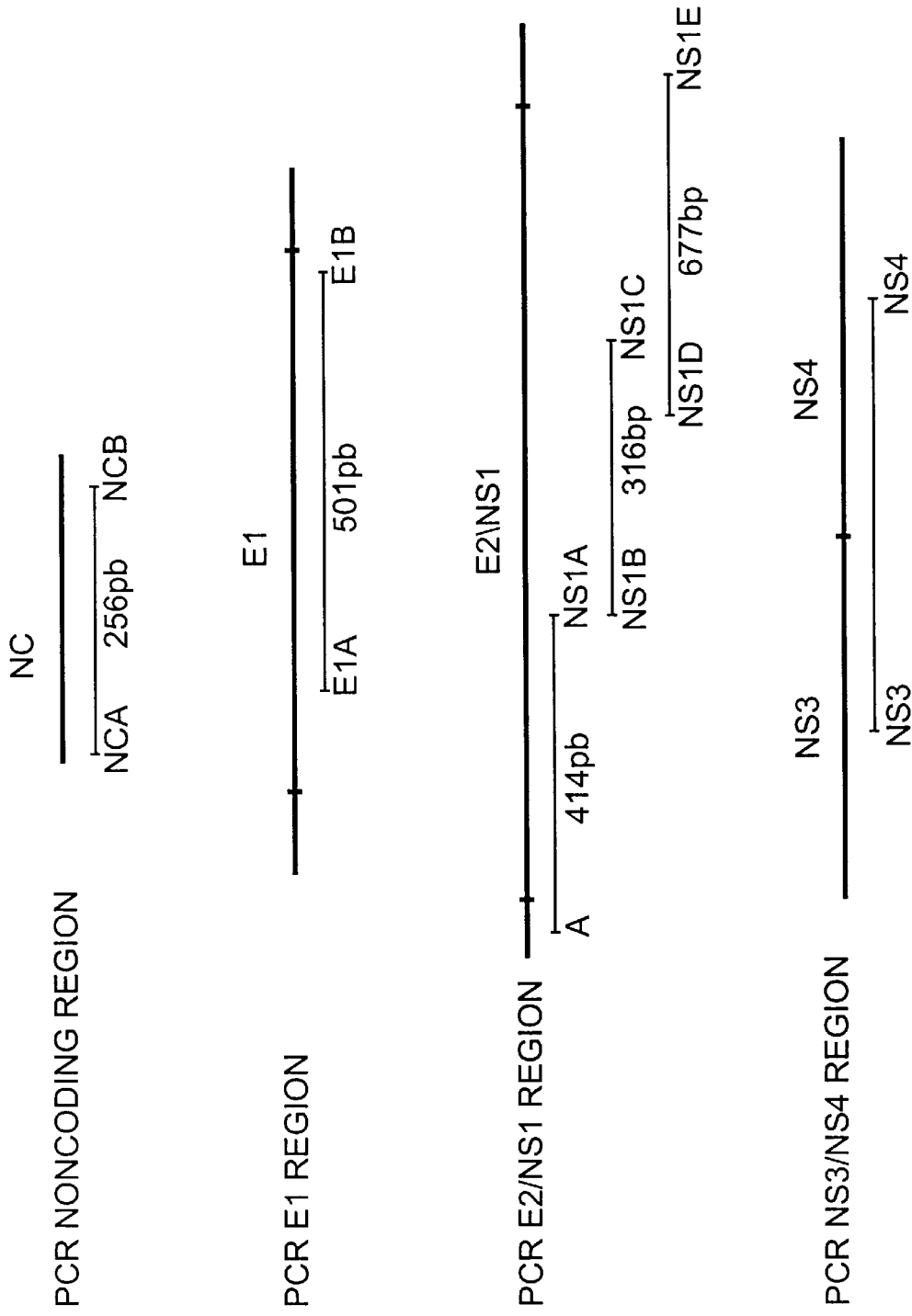

United States Patent [19]

Brechot et al.

[11] Patent Number: 5,919,454
[45] Date of Patent: Jul. 6, 1999

[54] NUCLEOTIDE AND PEPTIDE SEQUENCES OF A HEPATITIS C VIRUS ISOLATE, DIAGNOSTIC AND THERAPEUTIC APPLICATIONS

[75] Inventors: Christian Brechot; Dina Kremsdorf, both of Paris; Colette Porchon, Gentilly, all of France

[73] Assignee: Institut Pasteur, Paris, France

[21] Appl. No.: 08/487,231

[22] Filed: Jun. 7, 1995

Related U.S. Application Data

[62] Division of application No. 07/965,285, Mar. 18, 1993.

[51] Int. Cl.[6] .......................... G01N 33/53; A61K 39/29
[52] U.S. Cl. ..................................... 424/161.1; 424/139.1; 424/186.1; 424/189.1; 435/7.1; 435/69.3; 435/287.2; 435/326; 435/331; 435/339; 435/810; 530/387.1; 530/388.1; 530/388.3; 530/389.4; 530/391.1; 530/808

[58] Field of Search ................................ 436/501; 435/7.1, 435/810, 326, 331, 339, 287.2, 69.3; 530/387.1, 388.1, 388.3, 389.4, 391.1, 808; 424/139.1, 161.1, 186.1, 189.1

[56] References Cited

U.S. PATENT DOCUMENTS 5,350,671  9/1994  Houghton et al. .......................... 435/5

*Primary Examiner*—Laurie Scheiner
*Attorney, Agent, or Firm*—Finnegan, Henderson, Farabow, Garrett & Dunner, L.L.P.

[57] ABSTRACT

This invention relates to human or murine monoclonal antibodies specific for a peptide sequence of HCV E1, fragments of said monoclonal antibodies, hybridomas producing said monoclonal antibodies, in vitro diagnostic methods for detecting HCV E1-specific antigens in a biological sample, and diagnostic kits for detecting HCV E1-specific antigens in a biological sample.

12 Claims, 19 Drawing Sheets

```
1  CCATGGCGTTAGTATGAGTGTCGTACAGCCTTCCAGGACCCCCCCTCCCGGGAGAGCCATA  60
2  ................G...........................................  60
3  ................G...........................................  60
4  ................G...........................................  60

1  GTGGTCTGCGGAGCCGGTGAGTACACCGGAATTGCCAGGACGACCGGGTCCTTTCTTGGA  120
2  .....................A......................................  120
3  ............................................................  120
4  .....................A......................................  120

1  TCAACCCGCTCAATGCCTGGAGATTTGGGCGTGCCCCCGCAAGACTGCTAGCCGAGTAGT  180
2  .A..........................................C...............  180
3  .A..........................................C.....G.........  180
4  .A..........................................C.....G.........  180

1  GTTGGGTCGCGAAAGGCCTTGTGGTACTGCCCTGATAGGGTGCTTGCGAGTGCCCCGGGAG  240
2  ............................................................  240
3  ............................................................  240
4  ............................................................  240

1  GTCTCGTAGACCGTGC  256
2  ................  256
3  ................  256
4  ................  256
```

FIG. 2

```
1  TTCTGGAAGACGGCGTGAACTATGCAACAGGGAACCTTCCTGGTTGCTCTTTCTCTATCC   60
2  ............................................................   60
3  .........G..........................TT.G..C................T   60
4  ............................................................   60
5  .........G..........................T.G..C.................T   60

1  TCCTCCCTGGCCCTGCTCTCTTGCCTGAATTGCCCGGTCAGCCTACCAAGTACGCAATT    120
2  ...T.................T...........T.G..........G............  120
3  ...T...T....G..C.TT....CA.C..A..T..C..T..TG..........G....CG  120
4  ...T.................T...........T...............G..C......  120
5  ...T...TT...G..C.TT....CA.C..A..T..C..T..TG..........G....CG  120

1  CTCGCGGGCCTTTACCATGTCACCAATGATTGCCCTAACTCGAGTATTGTGTACGAGACGG  180
2  .CACG..G..............C..................G.............G...  180
3  TGTC...GA.A.............A..C..C..T.C.....A.C....T.......G... 180
4  .CACA..G....T.........................................G..C  180
5  TGTC...GA.A..............G..C..C..T.C.....A.C....T.......G.A 180

1  CCGATAGCATTCTACACTCTCCGGGTGTGTCCCTTGCGTTCGCGAGGTAACACCTCGA    240
2  ...GC..C..G...A............C.............T....C...G........CC 240
3  .G..CGTG..CA.G..TG.C..C...........C..G..C.....G...AAC..TT....CC 240
4  A...GC..C..G..TA.....................C..GT.............     240
5  .G..C.TG..CA.G..TA.................C..G..C.....G......AC....CC 240
```

*FIG. 3A*

```
1  AATGTTGGGTGGCGGTGGCCCCCTACAGTCGCCACCAGAGACGGCAGACTCCCCACAACGC  300
2  GG.........A..A.............G..G.....G..T..A.......G.G......  300
3  GT..C...A...C.CA.T.C..GC...GG...GA.T.C..CG.........T...A....  300
4  GG.........A..A.......C..G..A........G...A..........G.G.....  300
5  GT..C...A...C.CA.T.C..GC...GG...GA.T.C..CG.........T...A....  300

1  AGCTTCGACGTCATATCGATCTGCTCGTCGGGAGCGCCACCCTCTGCTCGGCCCTCTATG  360
2  ............C..........T..............T................C...  360
3  CAT.A....C..CG.....CT.......CG...T....CG..TG..TT.....C..TA.G..C.  360
4  ............C..........T..............T................C...  360
5  CAA.A....C..CG.....CT.......T....T....GCG..TG..TT........C..TA.G..C.  360

1  TGGGGGACTTGTGCGGGTCCGTCTTCCTCGTCGGTCAATTGTTCACCTTCTCCCCCAGGC  420
2  ......C.A.........T....T.....T................T............  420
3  ....TC.C....A..T..T.....A..TCC..GC..............G..TC.C....  420
4  ....TC..............TA.T....C.....T.........................  420
5  ....TC.C....A..T..T........TCC..GC..............G..TC.C....  420

1  GCCACTGGACAACGCAAGAGACTGCAACTGTTCCATCTACCCCGGCCACGTAACGGGTCACC  480
2  ........G........GT....T.C..T....T......TA..................  480
3  .G..TGA......GTA.G......C..A....T.......T...TA....T.A..C..T.  480
4  ........G........G.......T......T.......TA..................  480
5  .G..TGA......GT..G......C..A....T.......TT..T.A............  480
```

*FIG. 3B*

```
1  GCATGGCATGGGATATGATGA  501
2  ....................  501
3  .....T..............  501
4  ....................  501
5  .....T..............  501
```

FIG. 3C

```
1  LEDGVNYATGNLPGCSFSILLALLSCLTVPASAYQVRNSRGLYHVTNDCPNSSIVYETA   60
2  ............F.....................T.........I.E...VS.I...A.   60
3  ............F.......................................S...A.   60
4  ............F.....................T.........I.E...VS.I..AH   60
5  ............F.......................................S...A.   60

1  DSILHSPGCVPCVREGNTSKCWVAVAPTVATRDGRLPTTQLRRHIDLLVGSATLCSALYV  120
2  .A..T........AR..MT..............A..T.V.........T.AF....M..  120
3  .V.MA........N.S.R..LT..L.A.NASV....................       120
4  .A..T........V.R..MT..............A..TI.V........A.AF....M.  120
5  .M.MT........D.S.R..LT..L.A.NASV....................       120

1  GDLCGSVFLVGQLFTFSPRRHWTTQDCNCSIYPGHVTGHRMAWDMM              166
2  ...........IS..............G.........I..........              166
3  ...........I......E.V.............S.........              166
4  ............S..............G.........I..........              166
5  ..................E.V............LS.........              166
```

*FIG. 4*

```
1  AATGGCTCAACTGCTCAGGGTCCCGCAAGCCATCTTGGACATGATCGCTGTGCCCACTG   60
2  .......G..........C..A..A................T.................   60
3  .......G........C.CA..A....................T...............   60
4  GG..T.G..GT......C..A..A........TG..G.....G.G..G..G..G......   60
5  GG..T.G..GT.A....C..A..A........TG..A.....G.G..G..G..G......   60

1  GGGAGTCCTAGCGGGCATAGCGTATTTCTCCATGGTGGGAACTGGGCGAAGGTCCTGCT  120
2  ...........G..............................................G.  120
3  ...........G..............................................G.  120
4  ...........G.....C.T..C..C.AT........A.................T...A.  120
5  ...........G.....C.T..C..C.AT....................T.....TT..A.  120

1  AGTGCTGTTGCTGTTCGCCGGCGTCGATGCGGAAACCTACACCACCGGGGGAGTACTGC  180
2  ...........C...A..T........C.....C..GT.........A..G.C.G....  180
3  .................T................AT.GT.T.......ACAAG.C....  180
4  T...GC..C.A..C.........C..G.......GT.G........GCGG..CAG....  180
5  T...A..C.A..C..T.......T..C.G.C.T.....CG..GTG..G.......GTGCAA..G  180

1  CAGGACCACCGCAAGGACTCGTCAGCCTTTTCAGTCGAGGCGCCAAGCAGGACATCCAGCT  240
2  .CAC..TGT.TGT..TCT..T..T..T....CC..GCA.C.........A..G.......  240
3  .C.CG...T.TCT....T..T..T.C....CA.C.......T...A..............  240
4  .CAC....CTCCACG...CGTC..C....TCA.CT..G..GTCT..AGA...........  240
5  .CACGT..CTCTAC...ACGTC..C..T..A.CT..G..GTCC...A.A...T.......  240
```

*FIG. 5A*

```
1  GATCAACACCAACGGCAGCTGGCACATTAATCGCACAGCTTTGAACTGTAATGAGAGCCT  300
2  .............T........C.C..A...G..CC............T.........  300
3  .............T........C...A...G..C.............A.........  300
4  TG.G..T..............C...CA.G..T..CC.A..........C.....CTC..  300
5  TG.A..............T...C..CA.G..T..CC...........C......CTC..  300

1  CGACACCGGCTGGGTAGCGGGGCTCTTCTATTACCACAAATTCAACTCTTCAGGCTGCCC  360
2  TA..........T.G.A.....T....C.....G..........................T..  360
3  TA..........T.G.A.....TA.....C.A............GG........G...T..  360
4  .C....T.G.TCC.T..C.C..G.....CACA................G..C..G......  360
5  .C.A..T.G.TCC.T..C.C..G.....................................  325

1  CGAGAGGATGGCCAGCTGCAGACCCCTTGCCGATTTCGACCAGGGCTGGGGCCCTATCAG  420
2  T....C.A.............C..........A.....T..................  420
3  ......T..............C..G....A.......T....................  420
4  G...C.C...............CC...A...A.TGG...C.....A..........C  420
5  ......................................................... 325

1  TTATGCCAACGGAACCGGCCCCTGAACACCGGCCCCCTACTGCTGGCACTACCCCCAAAGCC  480
2  ..........................G..C.C.G.........................A..  480
3  .C........................G..C.C..A.........T.T.............A..  480
4  ........................G..T..GA.G..T........T...G.G..TCGA..  480
5  C...A.TG.GCCTGA.A.....G.T.GA.G..T..........T...G.G..TCGA..  325
```

FIG.5B

```
1  TTGTGGTATCGTGCCAGCACAGAGACCGTATGTGGCCCAGTGTATTGCTTCACTCCTAGCCC  540
2  ...C....T.....C..GA...GT..G....T.G.A...........C......         540
3  ...C..............C..A..G.......G.A.............C......         540
4  .....................A..C..GTC.CAG..G.......T.........C.A..    540
5  G..........................................................   325

1  CGTGGTGGGGACGACCAATAAGTTGGGCGCACCCACTTACAACTGGGGTTGTAATGA  600
2  ..........A......G.C.G..C.......G.......C....G........GAA...   600
3  ....................................................         541
4  ..T.........................................................   541
5  ............................................................   325

1  TACGGACGTCTTCGTCCTTAATAACACCAGGCCACCGCTGGGCAATTGGTTCGGCTGCAC  660
2  ...........................C..T...............T..T..         660
3  ....................................................         541
4  ....................................................         541
5  ....................................................         325

1  CTGGGTGAACTCATCTGGATTTACTAAAGTGTGCGGAGCGCCCTCCCTGTGTCATCGGAGG  720
2  ....A............A.....C..C.......................T...         720
3  ....................................................         541
4  ....................................................         541
5  ....................................................         325
```

FIG. 5C

```
1  AGCGGGCAATAACACCTTGTACTGCCCCACTGACTGTTCCGCAAGCATCCGGAAGCTAC      780
2  G...........C......C..C........T..C................C..C..      780
3                                                                  541
4                                                                  541
5                                                                  325

1  ATACTCCCGATGTGGCTCCGGTCCTTGGATCACGCCCAGGTGCCTGGTTGGCTATCCTTA     840
2  ......T..G..C.............C........A...........C..A....C..G..  840
3                                                                  541
4                                                                  541
5                                                                  325

1  TAGGCTCTGGCATTATCCCCTGTACTGTCAACTACACCCCTGTTCAAGGTCAGGATGTACGT   900
2  .......T................T.....CA.............A.A..T..AA......  900
3                                                                  541
4                                                                  541
5                                                                  325

1  GGGAGGGGTCGAGCACAGGCTGCAAGTCGCTTGCAACTGGACGCGGGGCGAGCGGTTGTAA    960
2  ...........A.........G...CT..C.....................A......CG.. 960
3                                                                  541
4                                                                  541
5                                                                  325
```

FIG. 5D

```
1  TCTGGACGACAGGGACACAGTGTCCGAGCTCAGTCCGCTGCTGTCTACCACACAGTGGCA    1020
2  .........A..................................C...T.A....A.C..T...    1020
3  ..............................................................    541
4  ..............................................................    541
5  ..............................................................    325

1  GGTCCCTCCCGTGTTCCTTTACGACCTTGCCAGCCCTTGACTACCGGCCTCATCCACCTCCA    1080
2  ...........................C..A...C.A........T.C...............    1080
3  ..............................................................    541
4  ..............................................................    541
5  ..............................................................    325

1  CCAGAACATCGTGGACGTGCAATATATTTGTACGGGGTCAAGCATTGTGTCCTGGGC    1140
2  ..........T.........G..C..........................C.C......    1140
3  ............................................................    541
4  ............................................................    541
5  ............................................................    325

1  CATCAAGTGGGAGTACGTCATTCTCCCTGTTTCTCCCTGCTTGCAGACGCGGCCGTCTGCTC    1200
2  ...T...............G......................C..T.................    1200
3  ..............................................................    541
4  ..............................................................    541
5  ..............................................................    325
```

FIG. 5E

```
1  CTGCTTGTGG . . . . . .  1210
2             . . . . . .  1210
3             . . . . . .   541
4             . . . . . .   541
5             . . . . . .   325
```

FIG. 5F

```
1   MAQLLRVPQAILDMIAGAHWGVLAGIAYFSMVGNWAKVLLLVLLLFAGV DAETYTTGGSTA    60
2   .......I............................V.................HV...AG   60
3   ...I................................V................IVS..QA.   60
4   VS..I...VV.V.......................L.Y............G...S..AAS    60
5   VS..I...VM.V.......................L.Y............GH.RV..VQG    60

1   RTTQGLVSLFSRGAKQDD QLINTNGSWHINRTALNCN ESLDTGWVAGLFYY HKFNSSGCP   120
2   H.VS.F...LAP......NV...............L.S....D.N...L....H.......  120
3   .AMS......TP.N.....S.....................N..L..I.Q...........  120
4   H..ST.A....P..S.R.V.....................D.H.FL.A....T.R......  120
5   HV.ST.T...RP..S.K..V....................D.Q..FL.A............  108

1   ERMASCRPLADFD QGWGPISYAN GTGPEHRPYCWHYPPKPCGIVPAQTVCGPVYCFTPSP   180
2   .L....T.......................S..DQ.........................KS   180
3   .L....R.T.............H..SA.DQ..............................KS   180
4   .M...IDW.A.........T.TEPDS.DQ.........A.R...................SQ   180
5   ..............................................................  108

1   VVVGTTNKLGAPTYNWGCNDTDVFVLNNTRPPLGNWFGCTWNSSGFTKVCGAPPCVIGG    240
2   .........DRS......S..E..................M..T..............    240
3   ...........................................................  180
4   ...........................................................  180
5   ...........................................................  108
```

*FIG. 6A*

```
1  AGNNTLYCPTDCFRKHPEATYSRCGSGPWITPRCLVGYPYRLMHYPCTVNYTLFKVRMYV    300
2  .....H..............D............................             300
3  .................................D.....I....I...              180
4  .........................................I....I...            180
5  ...................................................           108

1  GGVEHRLQVACNWTRGERCNLDDRDRSELSPLLLSTTQWVLPCSFTTLPALTTGLIHLH    360
2  ............EA...........D.E.........................       360
3  ....................................T.............S.        180
4  ...................................................         180
5  ...................................................         108

1  QNIVDVQYLYGVGSSIVSWAIKWEYVILLFLLLADARVCSCLW                  403
2  ..........................A......V.........                 180
3  ...........................................                 180
4  ...........................................                 180
5  ...........................................                 108
```

FIG. 6B

```
1   ACAATACGTGTGTCACCCAGACAGTCGACTTCAGCCTTGACCCTACCTTCACCATTGAAA    60
2   .........................T................................G.    60
3   ..GT..C..A.............T...G.........T.G..T..C...TC....C..G.    60

1   CAACAACGCTTCCCCAGGATGCTGTCTCCCGCACTCAACGTCGGGGCAGGACTGGCAGGG   120
2   ....TC....C.................................................   120
3   ..G..G..CG.G.........A......G..T.G......G..G..A..T..........   120

1   GGAAGCCAGGCATTTACAGATTTGTGGCACCTGGAGAGCGCCCCTCCGGCATGTTCGACT   180
2   ......................C..................G..G..............   180
3   ..C.G.AG........C..T..G........A.T..A.....A..G......G.CG...   180

1   CGTCCGTCCTCTGCGAGTGCTATGACGCAGGCTGTGCTTGGTATGAGCTCACGCCCGCCG   240
2   ...........................T............................T..   240
3   ..T.G....A..T.........T........G............................   240

1   AGACCACAGTCAGGCTACGAGCATACATGAACACCCCGGGACTTCCCGTGTGCCAAGACC   300
2   ....T...T.................G...............G................   300
3   ....T.G..T...T.G..G..T...C.A..T..A..A..GT.G.....C......G....   300
```

*FIG. 8A*

```
1   ATCTTGAGTTTTGGGAGGGCGTCTCTTCACGGGTCTCACCCATATAGACGCCCACTTCCTAT   360
2   .....A..............................T.A..C....T......T........   360
3   ........G....C......A...............A..C.......C......T.G....   360

1   CCCAGACAAAGCAGAGTGGGGAAAACCTTCCTTACCTGGTAGCGTACCAAGCCACCGTGT    420
2   ...........................G....................A.........    420
3   ........T.....GCA..A..C...T.C..C...........A...............    420

1   GCGCTAGGGCCCAAGCCCTCCCCGTCGTGGGACCAGATGTGGAAGTGCTTGATTCGTC      480
2   ..............T.........A..........................T......C.    480
3   .....C....TA.G.T.A.T.A........T..A...........TC.C..A..G.....   480

1   TCAAGCCCCACCCTCCATGGGCCAACACCCCCTGCTATACCGACTGGGCGCTGTTCAGAATG  540
2   ...............................A..............................  540
3   .A....T.G..G.C......G.......G..TA.G..A..A..C..C................  540

1   AAGTCACCCTGACGCACCCAATCACCAAATATATCATGACATGCATGTCGGCTGACCTGG    600
2   ..A..................G..........C..........................C....    600
3   ..G........C..A....T.A.........................................    569
```

*FIG. 8B*

```
1  AGGTCGTCACGAGTACCTGGGTGCTCGTGGGCGGCGTTCTGGCTGCTTTGGCCGCGTATT    660
2  .........................C...........T............C........    660
3  ............................................................    569

1  GCCTATCCACAGGCTGCGTGGTCATAGTAGGCAGGGTCATTTGTCCGGAAGCCGGCAA      720
2  ...G..A....................G................G.C..              720
3  ..................                                              569

1  TCATACCCGACAGGGAAGTCCTCTACCGGGAGTTCGATGAGATGAAGAGTGCTCTCAGC    780
2  .........T.....................A...........................    780
3  ............................................................    569

1  ACTTGCCATACACATCGAGCAAGGGATGATGCTCGCCCGAGCCAGTTCAAGCAGAAGGCCCTCG  840
2  ....A..G.....................................................    840
3  ..............................................................    569

1  GCCTCCCTGCAAACACGGTCCCGCCAGGAGGTCATCACCCCTGCTGTCCAGACCAACT    900
2  ........G..CGC........T........T...G.....                     900
3  .........                                                      569

1  GGCAGAGACTCGAGGGCCCTTCTGGGCGAAGCATATGTGGAACTT      943
2  ....A.A........A.............................     943
3  .............................................     569
```

FIG. 8C

| | | |
|---|---|---|
| 1 | NTCNVQTVDFSLDPTFTIETTLPQDAVSRTQRRGRTGRGKPGIYRFVAPGERPSGMFDS | 60 |
| 2 | .........I.................................................. | 60 |
| 3 | .....L....V...............RR.........T....A................. | 60 |
| 1 | SVLCECYDAGCAWYELTPAETTVRLRAYMNTPGLPVCQDHLEFWEGVFTGLTHIDAHFLS | 120 |
| 2 | ............................................................ | 120 |
| 3 | ..................S.........................S............... | 120 |
| 1 | QTKQSGENLPYLVAYQATVCARAQAPPPSWDQMWKCLIRLKPTLHGPTPLLYRLGAVQNE | 180 |
| 2 | ............................................................ | 180 |
| 3 | ....A.D.F..................K................................ | 180 |
| 1 | VTLTMPITKYIMTCMSADLEVVTSTWLVGGVLAALAAYCLSTGCVVIVGRVILSGKPAI | 240 |
| 2 | I....V...............................................V..... | 240 |
| 3 | ............ | 189 |
| 1 | IPDREVLYREFDEMEECSQHLPYIEQGMMLAEQFKQKALGLLQTRSRQAEVITPAVQTNW | 300 |
| 2 | ..........................................A.......A....E... | 300 |
| 3 | | 189 |
| 1 | QRLEAFWAKHMWN | 313 |
| 2 | .K..T........ | 313 |
| 3 | | 189 |

FIG. 9

SEQUENCE LISTING (1) GENERAL INFORMATION:

(iii) NUMBER OF SEQUENCES: 46

(2) INFORMATION FOR SEQ ID NO:1:

(i) SEQUENCE CHARACTERISTICS:
        (A) LENGTH: 256 base pairs
        (B) TYPE: nucleic acid
        (C) STRANDEDNESS: single
        (D) TOPOLOGY: linear (ii) MOLECULE TYPE: Other
        (A) DESCRIPTION: cDNA to genomic RNA (xi) SEQUENCE DESCRIPTION: SEQ ID NO:1:

```
CCATGGCGTT AGTATGAGTG TCGTACAGCC TCCAGGACCC CCCCTCCCGG GAGAGCCATA        60

GTGGTCTGCG GAGCCGGTGA GTACACCGGA ATTGCCAGGA CGACCGGGTC CTTTCTTGGA       120

TCAACCCGCT CAATGCCTGG AGATTTGGGC GTGCCCCCGC AAGACTGCTA GCCGAGTAGT       180

GTTGGGTCGC GAAAGGCCTT GTGGTACTGC CTGATAGGGT GCTTGCGAGT GCCCCGGGAG       240

GTCTCGTAGA CCGTGC                                                      256
```

(2) INFORMATION FOR SEQ ID NO:2:

(i) SEQUENCE CHARACTERISTICS:
        (A) LENGTH: 501 base pairs
        (B) TYPE: nucleic acid
        (C) STRANDEDNESS: single
        (D) TOPOLOGY: linear (ii) MOLECULE TYPE: Other
    (A) DESCRIPTION: cDNA to genomic RNA (xi) SEQUENCE DESCRIPTION: SEQ ID NO:2:

```
TTCTGGAAGA CGGCGTGAAC TATGCAACAG GGAACCTTCC TGGTTGCTCT TTCTCTATCC     60

TCCTCCTGGC CCTGCTCTCT TGCCTGACTG TGCCCGCGTC AGCCTACCAA GTACGCAATT    120

CTCGCGGCCT TTACCATGTC ACCAATGATT GCCCTAACTC GAGTATTGTG TACGAGACGG    180

CCGATAGCAT TCTACACTCT CCGGGGTGTG TCCCTTGCGT TCGCGAGGGT AACACCTCGA    240

AATGTTGGGT GGCGGTGGCC CCTACAGTCG CCACCAGAGA CGGCAGACTC CCCACAACGC    300

AGCTTCGACG TCATATCGAT CTGCTCGTCG GGAGCGCCAC CCTCTGCTCG GCCCTCTATG    360

TGGGGGACTT GTGCGGGTCC GTCTTCCTCG TCGGTCAATT GTTCACCTTC TCCCCCAGGC    420

GCCACTGGAC AACGCAAGAC TGCAACTGTT CCATCTACCC CGGCCACGTA ACGGGTCACC    480

GCATGGCATG GGATATGATG A                                             501
```

(2) INFORMATION FOR SEQ ID NO:3:

(i) SEQUENCE CHARACTERISTICS:
        (A) LENGTH: 166 amino acids
        (B) TYPE: amino acid
        (D) TOPOLOGY: linear (ii) MOLECULE TYPE: peptide (xi) SEQUENCE DESCRIPTION: SEQ ID NO:3:

```
Leu Glu Asp Gly Val Asn Tyr Ala Thr Gly Asn Leu Pro Gly Cys Ser
1               5                  10                  15

Phe Ser Ile Leu Leu Ala Leu Leu Ser Cys Leu Thr Val Pro Ala
            20                  25                  30

Ser Ala Tyr Gln Val Arg Asn Ser Arg Gly Leu Tyr His Val Thr Asn
            35                  40                  45

Asp Cys Pro Asn Ser Ser Ile Val Tyr Glu Thr Ala Asp Ser Ile Leu
    50                  55                  60

His Ser Pro Gly Cys Val Pro Cys Val Arg Glu Gly Asn Thr Ser Lys
65                  70                  75                  80

Cys Trp Val Ala Val Ala Pro Thr Val Ala Thr Arg Asp Gly Arg Leu
                85                  90                  95

Pro Thr Thr Gln Leu Arg Arg His Ile Asp Leu Leu Val Gly Ser Ala
            100                 105                 110

Thr Leu Cys Ser Ala Leu Tyr Val Gly Asp Leu Cys Gly Ser Val Phe
        115                 120                 125

Leu Val Gly Gln Leu Phe Thr Phe Ser Pro Arg Arg His Trp Thr Thr
    130                 135                 140

Gln Asp Cys Asn Cys Ser Ile Tyr Pro Gly His Val Thr Gly His Arg
145                 150                 155                 160

Met Ala Trp Asp Met Met
                165
```

(2) INFORMATION FOR SEQ ID NO:4:

(i) SEQUENCE CHARACTERISTICS:
        (A) LENGTH: 1210 base pairs
        (B) TYPE: nucleic acid
        (C) STRANDEDNESS: single
        (D) TOPOLOGY: linear (ii) MOLECULE TYPE: Other
        (A) DESCRIPTION: cDNA to genomic RNA (xi) SEQUENCE DESCRIPTION: SEQ ID NO:4:

```
AATGGCTCAA CTGCTCAGGG TCCCGCAAGC CATCTTGGAC ATGATCGCTG GTGCCCACTG     60
GGGAGTCCTA GCGGGCATAG CGTATTTCTC CATGGTGGGG AACTGGGCGA AGGTCCTGCT    120
AGTGCTGTTG CTGTTCGCCG GCGTCGATGC GGAAACCTAC ACCACCGGGG GGAGTACTGC    180
CAGGACCACG CAAGGACTCG TCAGCCTTTT CAGTCGAGGC GCCAAGCAGG ACATCCAGCT    240
GATCAACACC AACGGCAGCT GGCACATTAA TCGCACAGCT TTGAACTGTA ATGAGAGCCT    300
CGACACCGGC TGGGTAGCGG GGCTCTTCTA TTACCACAAA TTCAACTCTT CAGGCTGCCC    360
CGAGAGGATG GCCAGCTGCA GACCCCTTGC CGATTTCGAC CAGGGCTGGG GCCCTATCAG    420
TTATGCCAAC GGAACCGGCC CTGAACACCG CCCCTACTGC TGGCACTACC CCCCAAAGCC    480
TTGTGGTATC GTGCCAGCAC AGACCGTATG TGGCCCAGTG TATTGCTTCA CTCCTAGCCC    540
CGTGGTGGTG GGGACGACCA ATAAGTTGGG CGCACCCACT TACAACTGGG GTTGTAATGA    600
TACGGACGTC TTCGTCCTTA ATAACACCAG GCCACCGCTG GGCAATTGGT TCGGCTGCAC    660
CTGGGTGAAC TCATCTGGAT TTACTAAAGT GTGCGGAGCG CCTCCCTGTG TCATCGGAGG    720
AGCGGGCAAT AACACCTTGT ACTGCCCCAC TGACTGTTTC CGCAAGCATC CGGAAGCTAC    780
ATACTCCCGA TGTGGCTCCG GTCCTTGGAT CACGCCCAGG TGCCTGGTTG GCTATCCTTA    840
TAGGCTCTGG CATTATCCCT GTACTGTCAA CTACACCCTG TTCAAGGTCA GGATGTACGT    900
GGGAGGGGTC GAGCACAGGC TGCAAGTCGC TTGCAACTGG ACGCGGGGCG AGCGTTGTAA    960
TCTGGACGAC AGGGACAGGT CCGAGCTCAG TCCGCTGCTG CTGTCTACCA CACAGTGGCA   1020
GGTCCTCCCG TGTTCCTTTA CGACCTTGCC AGCCTTGACT ACCGGCCTCA TCCACCTCCA   1080
CCAGAACATC GTGGACGTGC AATATTTGTA CGGGGTGGGG TCAAGCATTG TGTCCTGGGC   1140
CATCAAGTGG GAGTACGTCA TTCTCCTGTT TCTCCTGCTT GCAGACGCGC GCGTCTGCTC   1200
CTGCTTGTGG                                                         1210
```

(2) INFORMATION FOR SEQ ID NO:5:

(i) SEQUENCE CHARACTERISTICS:
        (A) LENGTH: 403 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Met Ala Gln Leu Leu Arg Val Pro Gln Ala Ile Leu Asp Met Ile Ala
1               5                  10                  15

Gly Ala His Trp Gly Val Leu Ala Gly Ile Ala Tyr Phe Ser Met Val
            20                  25                  30

Gly Asn Trp Ala Lys Val Leu Leu Val Leu Leu Leu Phe Ala Gly Val
        35                  40                  45

Asp Ala Glu Thr Tyr Thr Thr Gly Gly Ser Thr Ala Arg Thr Thr Gln
    50                  55                  60

Gly Leu Val Ser Leu Phe Ser Arg Gly Ala Lys Gln Asp Ile Gln Leu
65                  70                  75                  80

Ile Asn Thr Asn Gly Ser Trp His Ile Asn Arg Thr Ala Leu Asn Cys
                85                  90                  95

Asn Glu Ser Leu Asp Thr Gly Trp Val Ala Gly Leu Phe Tyr Tyr His
            100                 105                 110

Lys Phe Asn Ser Ser Gly Cys Pro Glu Arg Met Ala Ser Cys Arg Pro
```

|     |     |     |     |     | 115 |     |     |     |     | 120 |     |     |     |     | 125 |     |     |
| --- | --- | --- | --- | --- | --- | --- | --- | --- | --- | --- | --- | --- | --- | --- | --- | --- | --- |
| Leu | Ala | Asp | Phe | Asp | Gln | Gly | Trp | Gly | Pro | Ile | Ser | Tyr | Ala | Asn | Gly |
|     | 130 |     |     |     |     | 135 |     |     |     |     | 140 |     |     |     |     |
| Thr | Gly | Pro | Glu | His | Arg | Pro | Tyr | Cys | Trp | His | Tyr | Pro | Pro | Lys | Pro |
| 145 |     |     |     |     | 150 |     |     |     |     | 155 |     |     |     |     | 160 |
| Cys | Gly | Ile | Val | Pro | Ala | Gln | Thr | Val | Cys | Gly | Pro | Val | Tyr | Cys | Phe |
|     |     |     |     | 165 |     |     |     |     | 170 |     |     |     |     | 175 |     |
| Thr | Pro | Ser | Pro | Val | Val | Gly | Thr | Thr | Asn | Lys | Leu | Gly | Ala | Pro |
|     |     |     | 180 |     |     |     |     | 185 |     |     |     |     | 190 |     |
| Thr | Tyr | Asn | Trp | Gly | Cys | Asn | Asp | Thr | Asp | Val | Phe | Val | Leu | Asn | Asn |
|     |     | 195 |     |     |     |     | 200 |     |     |     |     | 205 |     |     |     |
| Thr | Arg | Pro | Pro | Leu | Gly | Asn | Trp | Phe | Gly | Cys | Thr | Trp | Val | Asn | Ser |
| 210 |     |     |     |     | 215 |     |     |     |     | 220 |     |     |     |     |     |
| Ser | Gly | Phe | Thr | Lys | Val | Cys | Gly | Ala | Pro | Pro | Cys | Val | Ile | Gly | Gly |
| 225 |     |     |     |     | 230 |     |     |     |     | 235 |     |     |     |     | 240 |
| Ala | Gly | Asn | Asn | Thr | Leu | Tyr | Cys | Pro | Thr | Asp | Cys | Phe | Arg | Lys | His |
|     |     |     |     | 245 |     |     |     |     | 250 |     |     |     |     | 255 |     |
| Pro | Glu | Ala | Thr | Tyr | Ser | Arg | Cys | Gly | Ser | Gly | Pro | Trp | Ile | Thr | Pro |
|     |     |     | 260 |     |     |     |     | 265 |     |     |     |     | 270 |     |     |
| Arg | Cys | Leu | Val | Gly | Tyr | Pro | Tyr | Arg | Leu | Trp | His | Tyr | Pro | Cys | Thr |
|     |     |     | 275 |     |     |     |     | 280 |     |     |     |     | 285 |     |     |
| Val | Asn | Tyr | Thr | Leu | Phe | Lys | Val | Arg | Met | Tyr | Val | Gly | Gly | Val | Glu |
|     | 290 |     |     |     |     | 295 |     |     |     |     | 300 |     |     |     |     |
| His | Arg | Leu | Gln | Val | Ala | Cys | Asn | Trp | Thr | Arg | Gly | Glu | Arg | Cys | Asn |
| 305 |     |     |     |     | 310 |     |     |     |     | 315 |     |     |     |     | 320 |
| Leu | Asp | Asp | Arg | Asp | Arg | Ser | Glu | Leu | Ser | Pro | Leu | Leu | Leu | Ser | Thr |
|     |     |     |     | 325 |     |     |     |     | 330 |     |     |     |     | 335 |     |
| Thr | Gln | Trp | Gln | Val | Leu | Pro | Cys | Ser | Phe | Thr | Thr | Leu | Pro | Ala | Leu |
|     |     |     | 340 |     |     |     |     | 345 |     |     |     |     | 350 |     |     |
| Thr | Thr | Gly | Leu | Ile | His | Leu | His | Gln | Asn | Ile | Val | Asp | Val | Gln | Tyr |
|     |     |     | 355 |     |     |     |     | 360 |     |     |     |     | 365 |     |     |
| Leu | Tyr | Gly | Val | Gly | Ser | Ser | Ile | Val | Ser | Trp | Ala | Ile | Lys | Trp | Glu |
|     | 370 |     |     |     |     | 375 |     |     |     |     | 380 |     |     |     |     |
| Tyr | Val | Ile | Leu | Leu | Phe | Leu | Leu | Leu | Ala | Asp | Ala | Arg | Val | Cys | Ser |
| 385 |     |     |     |     | 390 |     |     |     |     | 395 |     |     |     |     | 400 |
| Cys | Leu | Trp |

(2) INFORMATION FOR SEQ ID NO:6:

(i) SEQUENCE CHARACTERISTICS:
        (A) LENGTH: 943 base pairs
        (B) TYPE: nucleic acid
        (C) STRANDEDNESS: single
        (D) TOPOLOGY: linear (ii) MOLECULE TYPE: Other
        (A) DESCRIPTION: cDNA to genomic RNA (xi) SEQUENCE DESCRIPTION: SEQ ID NO:6:

```
ACAATACGTG TGTCACCCAG ACAGTCGACT TCAGCCTTGA CCCTACCTTC ACCATTGAAA      60

CAACAACGCT TCCCCAGGAT GCTGTCTCCC GCACTCAACG TCGGGGCAGG ACTGGCAGGG     120

GGAAGCCAGG CATTTACAGA TTTGTGGCAC CTGGAGAGCG CCCCTCCGGC ATGTTCGACT     180

CGTCCGTCCT CTGCGAGTGC TATGACGCAG GCTGTGCTTG GTATGAGCTC ACGCCCGCCG     240

AGACCACAGT CAGGCTACGA GCATACATGA ACACCCCGGG ACTTCCCGTG TGCCAAGACC     300

ATCTTGAGTT TTGGGAGGGC GTCTTCACGG GTCTCACCCA TATAGACGCC CACTTCCTAT     360
```

```
CCCAGACAAA GCAGAGTGGG GAAAACCTTC CTTACCTGGT AGCGTACCAA GCCACCGTGT     420

GCGCTAGGGC CCAAGCCCCT CCCCCGTCGT GGGACCAGAT GTGGAAGTGC TTGATTCGTC     480

TCAAGCCCAC CCTCCATGGG CCAACACCCC TGCTATACCG ACTGGGCGCT GTTCAGAATG     540

AAGTCACCCT GACGCACCCA ATCACCAAAT ATATCATGAC ATGCATGTCG GCTGACCTGG     600

AGGTCGTCAC GAGTACCTGG GTGCTCGTGG GCGGCGTTCT GGCTGCTTTG GCCGCGTATT     660

GCCTATCCAC AGGCTGCGTG GTCATAGTAG GCAGGGTCAT TTTGTCCGGG AAGCCGGCAA     720

TCATACCCGA CAGGGAAGTC CTCTACCGGG AGTTCGATGA GATGGAAGAG TGCTCTCAGC     780

ACTTGCCATA CATCGAGCAA GGGATGATGC TCGCCGAGCA GTTCAAGCAG AAGGCCCTCG     840

GCCTCCTGCA AACACGGTCC CGCCAGGCAG AGGTCATCAC CCCTGCTGTC CAGACCAACT     900

GGCAGAGACT CGAGGCCTTC TGGGCGAAGC ATATGTGGAA CTT                      943
```

(2) INFORMATION FOR SEQ ID NO:7:

(i) SEQUENCE CHARACTERISTICS:
        (A) LENGTH: 313 amino acids
        (B) TYPE: amino acid
        (D) TOPOLOGY: linear (ii) MOLECULE TYPE: peptide (xi) SEQUENCE DESCRIPTION: SEQ ID NO:7:

```
Asn Thr Cys Val Thr Gln Thr Val Asp Phe Ser Leu Asp Pro Thr Phe
1               5                   10                  15

Thr Ile Glu Thr Thr Leu Pro Gln Asp Ala Val Ser Arg Thr Gln
            20                  25                  30

Arg Arg Gly Arg Thr Gly Arg Gly Lys Pro Gly Ile Tyr Arg Phe Val
        35                  40                  45

Ala Pro Gly Glu Arg Pro Ser Gly Met Phe Asp Ser Ser Val Leu Cys
    50                  55                  60

Glu Cys Tyr Asp Ala Gly Cys Ala Trp Tyr Glu Leu Thr Pro Ala Glu
65                  70                  75                  80

Thr Thr Val Arg Leu Arg Ala Tyr Met Asn Thr Pro Gly Leu Pro Val
                85                  90                  95

Cys Gln Asp His Leu Glu Phe Trp Glu Gly Val Phe Thr Gly Leu Thr
            100                 105                 110

His Ile Asp Ala His Phe Leu Ser Gln Thr Lys Gln Ser Gly Glu Asn
        115                 120                 125

Leu Pro Tyr Leu Val Ala Tyr Gln Ala Thr Val Cys Ala Arg Ala Gln
    130                 135                 140

Ala Pro Pro Pro Ser Trp Asp Gln Met Trp Lys Cys Leu Ile Arg Leu
145                 150                 155                 160

Lys Pro Thr Leu His Gly Pro Thr Pro Leu Leu Tyr Arg Leu Gly Ala
                165                 170                 175

Val Gln Asn Glu Val Thr Leu Thr His Pro Ile Thr Lys Tyr Ile Met
            180                 185                 190

Thr Cys Met Ser Ala Asp Leu Glu Val Val Thr Ser Thr Trp Val Leu
        195                 200                 205

Val Gly Gly Val Leu Ala Ala Leu Ala Ala Tyr Cys Leu Ser Thr Gly
    210                 215                 220

Cys Val Val Ile Val Gly Arg Val Ile Leu Ser Gly Lys Pro Ala Ile
225                 230                 235                 240

Ile Pro Asp Arg Glu Val Leu Tyr Arg Glu Phe Asp Glu Met Glu Glu
                245                 250                 255
```

Cys Ser Gln His Leu Pro Tyr Ile Glu Gln Gly Met Met Leu Ala Glu
            260                 265                 270

Gln Phe Lys Gln Lys Ala Leu Gly Leu Leu Gln Thr Arg Ser Arg Gln
        275                 280                 285

Ala Glu Val Ile Thr Pro Ala Val Gln Thr Asn Trp Gln Arg Leu Glu
290                 295                 300

Ala Phe Trp Ala Lys His Met Trp Asn
305                 310

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other
        (A) DESCRIPTION: DNA primer (xi) SEQUENCE DESCRIPTION: SEQ ID NO:8:

ACAATACGTG TGTCACC                                              17

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other
        (A) DESCRIPTION: DNA primer (xi) SEQUENCE DESCRIPTION: SEQ ID NO:9:

AAGTTCCACA TATGCTTCGC                                         20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other
        (A) DESCRIPTION: DNA primer (xi) SEQUENCE DESCRIPTION: SEQ ID NO:10:

TCCGTTGGCA TAACTGATAG                                         20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other
        (A) DESCRIPTION: DNA primer (xi) SEQUENCE DESCRIPTION: SEQ ID NO:11:

CTATCAGTTA TGCCAACGGA                                         20

(2) INFORMATION FOR SEQ ID NO:12:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: Other
    (A) DESCRIPTION: DNA primer (xi) SEQUENCE DESCRIPTION: SEQ ID NO:12:

GTTGCCCGCC CCTCCGATGT                                       20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other
        (A) DESCRIPTION: DNA primer (xi) SEQUENCE DESCRIPTION: SEQ ID NO:13:

CCCAGCCCCG TGGTGGTGGG                                       20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other
        (A) DESCRIPTION: DNA primer (xi) SEQUENCE DESCRIPTION: SEQ ID NO:14:

CCACAAGCAG GAGCAGACGC                                       20

(2) INFORMATION FOR SEQ ID NO:15:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Other
        (A) DESCRIPTION: DNA primer (xi) SEQUENCE DESCRIPTION: SEQ ID NO:15:

CCATGGCGTT AGTATGAGT                                        19

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Other
        (A) DESCRIPTION: DNA primer (xi) SEQUENCE DESCRIPTION: SEQ ID NO:16:

GCAGGTCTAC GAGACCTC                                         18

(2) INFORMATION FOR SEQ ID NO:17:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: Other
    (A) DESCRIPTION: DNA primer (xi) SEQUENCE DESCRIPTION: SEQ ID NO:17:

TTCTGGAAGA CGGCGTGAAC                                            20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other
        (A) DESCRIPTION: DNA primer (xi) SEQUENCE DESCRIPTION: SEQ ID NO:18:

TCATCATATC CCATGCCATG                                            20

(2) INFORMATION FOR SEQ ID NO:19:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: Other
        (A) DESCRIPTION: DNA probe (xi) SEQUENCE DESCRIPTION: SEQ ID NO:19:

CCTTCACCAT TGAGACAATC ACGCTCCCCC AGGATGCTGT                       40

(2) INFORMATION FOR SEQ ID NO:20:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: Other
        (A) DESCRIPTION: DNA probe (xi) SEQUENCE DESCRIPTION: SEQ ID NO:20:

CTGTCCTGAG AGGCTAGCCA GCTGCCGACC CCTTACCGAT                       40

(2) INFORMATION FOR SEQ ID NO:21:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: Other
        (A) DESCRIPTION: DNA probe (xi) SEQUENCE DESCRIPTION: SEQ ID NO:21:

AGGTCGGGCG CGCCCACCTA CAGCTGGGGT GAAAATGATA                       40

(2) INFORMATION FOR SEQ ID NO:22:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: Other
    (A) DESCRIPTION: DNA probe (xi) SEQUENCE DESCRIPTION: SEQ ID NO:22:

GTGCAGCCTC CAGGACCCCC                                        20

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other
        (A) DESCRIPTION: DNA probe (xi) SEQUENCE DESCRIPTION: SEQ ID NO:23:

CTCGTACACA ATACTCGAGT                                        20

(2) INFORMATION FOR SEQ ID NO:24:

(i) SEQUENCE CHARACTERISTICS:
        (A) LENGTH: 256 base pairs
        (B) TYPE: nucleic acid
        (C) STRANDEDNESS: single
        (D) TOPOLOGY: linear (ii) MOLECULE TYPE: Other
        (A) DESCRIPTION: cDNA to genomic RNA (xi) SEQUENCE DESCRIPTION: SEQ ID NO:24:

CCATGGCGTT AGTATGAGTG TCGTGCAGCC TCCAGGACCC CCCTCCCGG GAGAGCCATA    60

GTGGTCTGCG GAACCGGTGA GTACACCGGA ATTGCCAGGA CGACCGGGTC CTTTCTTGGA   120

TAAACCCGCT CAATGCCTGG AGATTTGGGC GCGCCCCCGC GAGACTGCTA GCCGAGTAGT   180

GTTGGGTCGC GAAAGGCCTT GTGGTACTGC CTGATAGGGT GCTTGCGAGT GCCCCGGGAG   240

GTCTCGTAGA CCGTGC                                                  256

(2) INFORMATION FOR SEQ ID NO:25:

(i) SEQUENCE CHARACTERISTICS:
        (A) LENGTH: 256 base pairs
        (B) TYPE: nucleic acid
        (C) STRANDEDNESS: single
        (D) TOPOLOGY: linear (ii) MOLECULE TYPE: Other
        (A) DESCRIPTION: cDNA to genomic RNA (xi) SEQUENCE DESCRIPTION: SEQ ID NO:25:

CCATGGCGTT AGTATGAGTG TCGTGCAGCC TCCAGGACCC CCCTCCCGG GAGAGCCATA    60

GTGGTCTGCG GAGCCGGTGA GTACACCGGA ATTGCCAGGA CGACCGGGTC CTTTCTTGGA   120

TAAACCCGCT CAATGCCTGG AGATTTGGGC GCGCCCCCGC AAGACTGCTA GCCGAGTAGT   180

GTTGGGTCGC GAAAGGCCTT GTGGTACTGC CTGATAGGGT GCTTGCGAGT GCCCCGGGAG   240

GTCTCGTAGA CCGTGC                                                  256

(2) INFORMATION FOR SEQ ID NO:26:

(i) SEQUENCE CHARACTERISTICS:
            (A) LENGTH: 256 base pairs
            (B) TYPE: nucleic acid
            (C) STRANDEDNESS: single
            (D) TOPOLOGY: linear (ii) MOLECULE TYPE: Other
            (A) DESCRIPTION: cDNA to genomic RNA (xi) SEQUENCE DESCRIPTION: SEQ ID NO:26:

CCATGGCGTT AGTATGAGTG TCGTGCAGCC TCCAGGACCC CCCCTCCCGG GAGAGCCATA      60

GTGGTCTGCG GAACCGGTGA GTACACCGGA ATTGCCAGGA CGACCGGGTC CTTTCTTGGA     120

TAAACCCGCT CAATGCCTGG AGATTTGGGC GCGCCCCCGC GAGACTGCTA GCCGAGTAGT     180

GTTGGGTCGC GAAAGGCCTT GTGGTACTGC CTGATAGGGT GCTTGCGAGT GCCCCGGGAG     240

GTCTCGTAGA CCGTGC                                                    256

(2) INFORMATION FOR SEQ ID NO:27:

(i) SEQUENCE CHARACTERISTICS:
            (A) LENGTH: 501 base pairs
            (B) TYPE: nucleic acid
            (C) STRANDEDNESS: single
            (D) TOPOLOGY: linear (ii) MOLECULE TYPE: Other
            (A) DESCRIPTION: cDNA to genomic RNA (xi) SEQUENCE DESCRIPTION: SEQ ID NO:27:

TTCTGGAAGA CGGCGTGAAC TATGCAACAG GAACCTTCC TGGTTGCTCT TTCTCTATCT       60

TCCTTCTGGC CCTGCTCTCT TGCTTGACTG TGCCCGCTTC GGCCTACCAA GTGCGCAATT     120

CCACGGGGCT TTACCACGTC ACCAATGATT GCCCTAACTC GAGTATTGTG TACGAGGCGG     180

CCGATGCCAT CCTGCACACT CCGGGGTGCG TCCCTTGCGT TCGTGAGGGC AACGCCTCGA     240

GGTGTTGGGT GGCGATGACC CCTACGGTGG CCACCAGGGA TGGAAGACTC CCCGCGACGC     300

AGCTTCGACG TCACATCGAT CTGCTTGTCG GGAGCGCCAC CCTCTGTTCG GCCCTCTACG     360

TGGGGGACCT ATGCGGGTCT GTCTTTCTTG TCGGCCAATT GTTCACCTTC TCTCCCAGGC     420

GCCACTGGAC GACGCAAGGT TGCAATTGCT CTATCTATCC CGGCCATATA ACGGGTCACC     480

GCATGGCATG GGATATGATG A                                              501

(2) INFORMATION FOR SEQ ID NO:28:

(i) SEQUENCE CHARACTERISTICS:
            (A) LENGTH: 501 base pairs
            (B) TYPE: nucleic acid
            (C) STRANDEDNESS: single
            (D) TOPOLOGY: linear (ii) MOLECULE TYPE: Other
            (A) DESCRIPTION: cDNA to genomic RNA (xi) SEQUENCE DESCRIPTION: SEQ ID NO:28:

TTCTGGAGGA CGGCGTGAAC TATGCAACAG GAATTTGCC CGGTTGCTCT TTCTCTATCT       60

TCCTCTTGGC TCTGCTGTCC TGTTTGACCA TCCCAGCTTC CGCTTATGAA GTGCGCAACG     120

TGTCCGGGAT ATACCATGTC ACAAACGACT GCTCCAACTC AAGCATTGTG TATGAGGCGG     180

CGGACGTGAT CATGCATGCC CCCGGGTGCG TGCCCTGCGT TCGGGAGAAC AATTCCTCCC     240

GTTGCTGGGT AGCGCTCACT CCCACGCTCG CGGCCAGGAA TGCCAGCGTC CCCACTACGA     300

CATTACGACG CCACGTCGAC TTGCTCGTTG GGACGGCTGC TTTCTGCTCC GCTATGTACG     360

TGGGGGATCT CTGCGGATCT GTTTTCCTCA TCTCCCAGCT GTTCACCTTC TCGCCTCGCC     420

```
GGCATGAGAC AGTACAGGAC TGCAACTGCT CAATCTATCC CGGCCACGTA TCAGGCCATC      480

GCATGGCTTG GGATATGATG A                                                501
```

(2) INFORMATION FOR SEQ ID NO:29:

(i) SEQUENCE CHARACTERISTICS:
        (A) LENGTH: 501 base pairs
        (B) TYPE: nucleic acid
        (C) STRANDEDNESS: single
        (D) TOPOLOGY: linear (ii) MOLECULE TYPE: Other
        (A) DESCRIPTION: cDNA to genomic RNA (xi) SEQUENCE DESCRIPTION: SEQ ID NO:29:

```
TTCTGGAAGA CGGCGTGAAC TATGCAACAG GGAACCTTCC TGGTTGCTCT TTCTCTATCT       60

TCCTTCTGGC CCTGCTCTCT TGCCTGACTG TGCCCGCTTC AGCCTACCAA GTGCGCAACT      120

CCACAGGGCT TTATCATGTC ACCAATGATT GCCCTAACTC GAGTATTGTG TACGAGGCGC      180

ACGATGCCAT CCTGCATACT CCGGGGTGTG TCCCTTGCGT TCGCGAGGGC AACGTCTCGA      240

GGTGTTGGGT GGCGATGACC CCCACGGTAG CCACCAGGGA CGGAAGACTC CCCGCGACGC      300

AGCTTCGACG TCACATCGAT CTGCTTGTCG GGAGCGCCAC CCTCTGTTCG GCCCTCTACG      360

TGGGGGATCT GTGCGGGTCC GTCTTCCTTA TTGGTCAACT GTTTACCTTC TCTCCCAGGC      420

GCCACTGGAC AACGCAAGGC TGCAATTGTT CTATCTACCC CGGCCATATA ACGGGTCATC      480

GCATGGCATG GGATATGATG A                                                501
```

(2) INFORMATION FOR SEQ ID NO:30:

(i) SEQUENCE CHARACTERISTICS:
        (A) LENGTH: 501 base pairs
        (B) TYPE: nucleic acid
        (C) STRANDEDNESS: single
        (D) TOPOLOGY: linear (ii) MOLECULE TYPE: Other
        (A) DESCRIPTION: cDNA to genomic RNA (xi) SEQUENCE DESCRIPTION: SEQ ID NO:30:

```
TTCTGGAGGA CGGCGTGAAC TATGCAACAG GGAACTTGCC CGGTTGCTCT TTCTCTATCT       60

TCCTCTTGGC TTTGCTGTCC TGTTTGACCA TCCCAGCTTC CGCTTATGAA GTGCGCAACG      120

TGTCCGGGAT ATACCATGTC ACGAACGACT GCTCCAACTC AAGCATTGTG TATGAGGCAG      180

CGGACATGAT CATGCATACT CCCGGGTGCG TGCCCTGCGT TCGGGAGGAC AACAGCTCCC      240

GTTGCTGGGT AGCGCTCACT CCCACGCTCG CGGCCAGGAA TGCCAGCGTC CCCACTACGA      300

CAATACGACG CCACGTCGAC TTGCTCGTTG GGGCGGCTGC TTTCTGCTCC GCTATGTACG      360

TGGGGGATCT CTGCGGATCT GTTTTCCTCG TCTCCCAGCT GTTCACCTTC TCGCCTCGCC      420

GGCATGAGAC AGTGCAGGAC TGCAACTGCT CAATCTATCC CGGCCATTTA TCAGGTCACC      480

GCATGGCTTG GGATATGATG A                                                501
```

(2) INFORMATION FOR SEQ ID NO:31:

(i) SEQUENCE CHARACTERISTICS:
        (A) LENGTH: 166 amino acids
        (B) TYPE: amino acid
        (D) TOPOLOGY: linear (ii) MOLECULE TYPE: peptide (xi) SEQUENCE DESCRIPTION: SEQ ID NO:31:

```
Leu Glu Asp Gly Val Asn Tyr Ala Thr Gly Asn Leu Pro Gly Cys Ser
 1               5                  10                  15

Phe Ser Ile Phe Leu Leu Ala Leu Leu Ser Cys Leu Thr Val Pro Ala
            20                  25                  30

Ser Ala Tyr Gln Val Arg Asn Ser Thr Gly Leu Tyr His Val Thr Asn
            35                  40                  45

Asp Cys Pro Asn Ser Ser Ile Val Tyr Glu Ala Ala Asp Ala Ile Leu
        50                  55                  60

His Thr Pro Gly Cys Val Pro Cys Val Arg Glu Gly Asn Ala Ser Arg
65                  70                  75                  80

Cys Trp Val Ala Met Thr Pro Thr Val Ala Thr Arg Asp Gly Arg Leu
                85                  90                  95

Pro Ala Thr Gln Leu Arg Arg His Ile Asp Leu Leu Val Gly Ser Ala
                100                 105                 110

Thr Leu Cys Ser Ala Leu Tyr Val Gly Asp Leu Cys Gly Ser Val Phe
            115                 120                 125

Leu Val Gly Gln Leu Phe Thr Phe Ser Pro Arg Arg His Trp Thr Thr
130                 135                 140

Gln Gly Cys Asn Cys Ser Ile Tyr Pro Gly His Ile Thr Gly His Arg
145                 150                 155                 160

Met Ala Trp Asp Met Met
                165

(2) INFORMATION FOR SEQ ID NO:32:

(i) SEQUENCE CHARACTERISTICS:
        (A) LENGTH: 166 amino acids
        (B) TYPE: amino acid
        (D) TOPOLOGY: linear (ii) MOLECULE TYPE: peptide (xi) SEQUENCE DESCRIPTION: SEQ ID NO:32:

Leu Glu Asp Gly Val Asn Tyr Ala Thr Gly Asn Leu Pro Gly Cys Ser
 1               5                  10                  15

Phe Ser Ile Phe Leu Leu Ala Leu Leu Ser Cys Leu Thr Ile Pro Ala
            20                  25                  30

Ser Ala Tyr Glu Val Arg Asn Val Ser Gly Ile Tyr His Val Thr Asn
            35                  40                  45

Asp Cys Ser Asn Ser Ser Ile Val Tyr Glu Ala Ala Asp Val Ile Met
        50                  55                  60

His Ala Pro Gly Cys Val Pro Cys Val Arg Glu Asn Asn Ser Ser Arg
65                  70                  75                  80

Cys Trp Val Ala Leu Thr Pro Thr Leu Ala Arg Asn Ala Ser Val
                85                  90                  95

Pro Thr Thr Thr Leu Arg Arg His Val Asp Leu Leu Val Gly Thr Ala
                100                 105                 110

Ala Phe Cys Ser Ala Met Tyr Val Gly Asp Leu Cys Gly Ser Val Phe
            115                 120                 125

Leu Ile Ser Gln Leu Phe Thr Phe Ser Pro Arg Arg His Glu Thr Val
130                 135                 140

Gln Asp Cys Asn Cys Ser Ile Tyr Pro Gly His Val Ser Gly His Arg
145                 150                 155                 160

Met Ala Trp Asp Met Met
                165
```

(2) INFORMATION FOR SEQ ID NO:33:

(i) SEQUENCE CHARACTERISTICS:
        (A) LENGTH: 166 amino acids
        (B) TYPE: amino acid
        (D) TOPOLOGY: linear (ii) MOLECULE TYPE: peptide (xi) SEQUENCE DESCRIPTION: SEQ ID NO:33:

```
Leu Glu Asp Gly Val Asn Tyr Ala Thr Gly Asn Leu Pro Gly Cys Ser
 1               5                  10                  15

Phe Ser Ile Phe Leu Leu Ala Leu Leu Ser Cys Leu Thr Val Pro Ala
            20                  25                  30

Ser Ala Tyr Gln Val Arg Asn Ser Thr Gly Leu Tyr His Val Thr Asn
        35                  40                  45

Asp Cys Pro Asn Ser Ser Ile Val Tyr Glu Ala His Asp Ala Ile Leu
    50                  55                  60

His Thr Pro Gly Cys Val Pro Cys Val Arg Glu Gly Asn Val Ser Arg
65                  70                  75                  80

Cys Trp Val Ala Met Thr Pro Thr Val Ala Thr Arg Asp Gly Arg Leu
                85                  90                  95

Pro Ala Thr Gln Leu Arg Arg His Ile Asp Leu Leu Val Gly Ser Ala
                100                 105                 110

Thr Leu Cys Ser Ala Leu Tyr Val Gly Asp Leu Cys Gly Ser Val Phe
            115                 120                 125

Leu Ile Gly Gln Leu Phe Thr Phe Ser Pro Arg Arg His Trp Thr Thr
        130                 135                 140

Gln Gly Cys Asn Cys Ser Ile Tyr Pro Gly His Ile Thr Gly His Arg
145                 150                 155                 160

Met Ala Trp Asp Met Met
                165
```

(2) INFORMATION FOR SEQ ID NO:34:

(i) SEQUENCE CHARACTERISTICS:
        (A) LENGTH: 166 amino acids
        (B) TYPE: amino acid
        (D) TOPOLOGY: linear (ii) MOLECULE TYPE: peptide (xi) SEQUENCE DESCRIPTION: SEQ ID NO:34:

```
Leu Glu Asp Gly Val Asn Tyr Ala Thr Gly Asn Leu Pro Gly Cys Ser
 1               5                  10                  15

Phe Ser Ile Phe Leu Leu Ala Leu Leu Ser Cys Leu Thr Ile Pro Ala
            20                  25                  30

Ser Ala Tyr Glu Val Arg Asn Val Ser Gly Ile Tyr His Val Thr Asn
        35                  40                  45

Asp Cys Ser Asn Ser Ser Ile Val Tyr Glu Ala Ala Asp Met Ile Met
    50                  55                  60

His Thr Pro Gly Cys Val Pro Cys Val Arg Glu Asp Asn Ser Ser Arg
65                  70                  75                  80

Cys Trp Val Ala Leu Thr Pro Thr Leu Ala Ala Arg Asn Ala Ser Val
                85                  90                  95

Pro Thr Thr Thr Ile Arg Arg His Val Asp Leu Leu Val Gly Ala Ala
                100                 105                 110

Ala Phe Cys Ser Ala Met Tyr Val Gly Asp Leu Cys Gly Ser Val Phe
            115                 120                 125
```

```
Leu Val Ser Gln Leu Phe Thr Phe Ser Pro Arg Arg His Glu Thr Val
130                 135                 140

Gln Asp Cys Asn Cys Ser Ile Tyr Pro Gly His Leu Ser Gly His Arg
145                 150                 155                 160

Met Ala Trp Asp Met Met
                165
```

(2) INFORMATION FOR SEQ ID NO:35:

(i) SEQUENCE CHARACTERISTICS:
        (A) LENGTH: 1210 base pairs
        (B) TYPE: nucleic acid
        (C) STRANDEDNESS: single
        (D) TOPOLOGY: linear (ii) MOLECULE TYPE: Other
        (A) DESCRIPTION: cDNA to genomic RNA (xi) SEQUENCE DESCRIPTION: SEQ ID NO:35:

```
AATGGCTCAG CTGCTCCGGA TCCCACAAGC CATCTTGGAC ATGATCGCTG GTGCTCACTG      60
GGGAGTCCTG GCGGGCATAG CGTATTTCTC CATGGTGGGG AACTGGGCGA AGGTCCTGGT     120
AGTGCTGCTG CTATTTGCCG GCGTCGACGC GGAAACCCAC GTCACCGGGG AAGTGCCGG      180
CCACACTGTG TCTGGATTTG TTAGCCTCCT CGCACCAGGC GCCAAGCAGA ACGTCCAGCT     240
GATCAACACC AACGGCAGTT GGCACCTCAA TAGCACGGCT CTGAACTGCA ATGATAGCCT     300
TAACACCGGC TGGTTGGCAG GCTTTTCTA TCACCACAAG TTCAACTCTT CAGGCTGTCC      360
TGAGAGGCTA GCCAGCTGCC GACCCCTTAC CGATTTTGAC CAGGGCTGGG GCCCTATCAG     420
TTATGCCAAC GGAAGCGGCC CCGACCAGCG CCCCTACTGC TGGCACTACC CCCCAAAACC     480
TTGCGGTATT GTGCCCGCGA AGAGTGTGTG TGGTCCGGTA TATTGCTTCA CTCCCAGCCC     540
CGTGGTGGTG GGAACGACCG ACAGGTCGGG CGCGCCCACC TACAGCTGGG GTGAAAATGA     600
TACGGACGTC TTCGTCCTTA ACAATACCAG GCCACCGCTG GGCAATTGGT TCGGTTGTAC     660
CTGGATGAAC TCAACTGGAT TCACCAAAGT GTGCGGAGCG CCTCCTTGTG TCATCGGAGG     720
GGCGGGCAAC AACACCCTGC ACTGCCCCAC TGATTGCTTC CGCAAGCATC CGGACGCCAC     780
ATACTCTCGG TGCGGCTCCG GTCCCTGGAT CACACCCAGG TGCCTGGTCG ACTACCCGTA     840
TAGGCTTTGG CATTATCCTT GTACCATCAA CTACACCATA TTTAAAATCA GGATGTACGT     900
GGGAGGGGTC GAACACAGGC TGGAAGCTGC CTGCAACTGG ACGCGGGGCG AACGTTGCGA     960
TCTGGAAGAC AGGGACAGGT CCGAGCTCAG CCCGTTACTG CTGACCACTA CACAGTGGCA    1020
GGTCCTCCCG TGTTCCTTCA CAACCCTACC AGCCTTGTCC ACCGGCCTCA TCCACCTCCA    1080
CCAGAACATT GTGGACGTGC AGTACTTGTA CGGGGTGGGG TCAAGCATCG CGTCCTGGGC    1140
CATTAAGTGG GAGTACGTCG TTCTCCTGTT CCTTCTGCTT GCAGACGCGC GCGTCTGCTC    1200
CTGCTTGTGG                                                          1210
```

(2) INFORMATION FOR SEQ ID NO:36:

(i) SEQUENCE CHARACTERISTICS:
        (A) LENGTH: 541 base pairs
        (B) TYPE: nucleic acid
        (C) STRANDEDNESS: single
        (D) TOPOLOGY: linear (ii) MOLECULE TYPE: Other
        (A) DESCRIPTION: cDNA to genomic RNA (xi) SEQUENCE DESCRIPTION: SEQ ID NO:36:

```
AATGGCTCAG CTGCTCCGCA TCCCACAAGC CATCTTGGAT ATGATCGCTG GTGCTCACTG      60
```

```
GGGAGTCCTG GCGGGCATAG CGTATTTCTC CATGGTGGGG AACTGGGCGA AGGTCCTGGT        120

AGTGCTGTTG CTGTTTGCCG GCGTCGACGC GGAAACCATC GTCTCCGGGG ACAAGCCGC         180

CCGCGCCATG TCTGGACTTG TTAGTCTCTT CACACCAGGC GCTAAGCAGA ACATCCAGCT        240

GATCAACACC AACGGCAGTT GGCACATCAA TAGCACGGCC TTGAACTGCA ATGAAAGCCT        300

TAACACCGGC TGGTTAGCAG GCTTATCTA TCAACACAAA TTCAACTCTT CGGGCTGTCC         360

CGAGAGGTTG GCCAGCTGCC GACGCCTTAC CGATTTTGAC CAGGGCTGGG GCCCTATCAG        420

TCATGCCAAC GGAAGCGGCC CCGACCAACG CCCCTATTGT TGGCACTACC CCCCAAAACC       480

TTGCGGTATC GTGCCCGCAA AGAGCGTATG TGGCCCGGTA TATTGCTTCA CTCCCAGCCC       540

C                                                                        541
```

(2) INFORMATION FOR SEQ ID NO:37:

(i) SEQUENCE CHARACTERISTICS:
      (A) LENGTH: 541 base pairs
      (B) TYPE: nucleic acid
      (C) STRANDEDNESS: single
      (D) TOPOLOGY: linear (ii) MOLECULE TYPE: Other
      (A) DESCRIPTION: cDNA to genomic RNA (xi) SEQUENCE DESCRIPTION: SEQ ID NO:37:

```
GGTGTCGCAG TTGCTCCGGA TCCCACAAGC TGTCGTGGAC ATGGTGGCGG GGGCCCACTG         60

GGGAGTCCTG GCGGGCCTTG CCTACTATTC CATGGTAGGG AACTGGGCTA AGGTCCTGAT        120

TGTGGCGCTA CTCTTCGCCG GCGTTGACGG GGAGACCTAC ACGTCGGGGG GGGCGGCCAG        180

CCACACCACC TCCACGCTCG CGTCCCTCTT CTCACCTGGG GCGTCTCAGA GAATCCAGCT        240

TGTGAATACC AACGGCAGCT GGCACATCAA CAGGACTGCC CTAAACTGCA ATGACTCCCT        300

CCACACTGGG TTCCTTGCCG CGCTGTTCTA CACACACAGG TTCAACTCGT CCGGGTGCCC        360

GGAGCGCATG GCCAGCTGCC GCCCCATTGA CTGGTTCGCC CAGGGATGGG GCCCCATCAC        420

CTATACTGAG CCTGACAGCC CGGATCAGAG GCCTTATTGC TGGCATTACG CGCCTCGACC       480

GTGTGGTATC GTACCCGCGT CGCAGGTGTG TGGTCCAGTG TATTGCTTCA CCCCAAGCCC       540

T                                                                        541
```

(2) INFORMATION FOR SEQ ID NO:38:

(i) SEQUENCE CHARACTERISTICS:
      (A) LENGTH: 325 base pairs
      (B) TYPE: nucleic acid
      (C) STRANDEDNESS: single
      (D) TOPOLOGY: linear (ii) MOLECULE TYPE: Other
      (A) DESCRIPTION: cDNA to genomic RNA (xi) SEQUENCE DESCRIPTION: SEQ ID NO:38:

```
GGTGTCGCAG TTACTCCGGA TCCCACAAGC TGTCATGGAC ATGGTGGCGG GGGCCCACTG         60

GGGAGTCCTA GCGGGCCTTG CCTACTATTC CATGGTGGGG AACTGGGCTA AGGTTTTGAT        120

TGTGATGCTA CTCTTTGCCG GCGTTGACGG GCATACCCGC GTGACGGGGG GGGTGCAAGG       180

CCACGTCACC TCTACACTCA CGTCCCTCTT TAGACCTGGG GCGTCCCAGA AAATTCAGCT        240

TGTAAACACC AATGGCAGTT GGCATATCAA CAGGACTGCC CTGAACTGCA ATGACTCCCT        300

CCAAACTGGG TTCCTTGCCG CGCTG                                              325
```

(2) INFORMATION FOR SEQ ID NO:39:

(i) SEQUENCE CHARACTERISTICS:
  (A) LENGTH: 403 amino acids
  (B) TYPE: amino acid
  (D) TOPOLOGY: linear (ii) MOLECULE TYPE: peptide (xi) SEQUENCE DESCRIPTION: SEQ ID NO:39:

```
Met Ala Gln Leu Leu Arg Ile Pro Gln Ala Ile Leu Asp Met Ile Ala
1               5                   10                  15

Gly Ala His Trp Gly Val Leu Ala Gly Ile Ala Tyr Phe Ser Met Val
                20                  25                  30

Gly Asn Trp Ala Lys Val Leu Val Leu Leu Leu Phe Ala Gly Val
            35                  40                  45

Asp Ala Glu Thr His Val Thr Gly Gly Ser Ala Gly His Thr Val Ser
50                  55                  60

Gly Phe Val Ser Leu Leu Ala Pro Gly Ala Lys Gln Asn Val Gln Leu
65                  70                  75                  80

Ile Asn Thr Asn Gly Ser Trp His Leu Asn Ser Thr Ala Leu Asn Cys
                85                  90                  95

Asn Asp Ser Leu Asn Thr Gly Trp Leu Ala Gly Leu Phe Tyr His His
                100                 105                 110

Lys Phe Asn Ser Ser Gly Cys Pro Glu Arg Leu Ala Ser Cys Arg Pro
            115                 120                 125

Leu Thr Asp Phe Asp Gln Gly Trp Gly Pro Ile Ser Tyr Ala Asn Gly
            130                 135                 140

Ser Gly Pro Asp Gln Arg Pro Tyr Cys Trp His Tyr Pro Pro Lys Pro
145                 150                 155                 160

Cys Gly Ile Val Pro Ala Lys Ser Val Cys Gly Pro Val Tyr Cys Phe
                165                 170                 175

Thr Pro Ser Pro Val Val Gly Thr Thr Asp Arg Ser Gly Ala Pro
                180                 185                 190

Thr Tyr Ser Trp Gly Glu Asn Asp Thr Asp Val Phe Val Leu Asn Asn
            195                 200                 205

Thr Arg Pro Pro Leu Gly Asn Trp Phe Gly Cys Thr Trp Met Asn Ser
210                 215                 220

Thr Gly Phe Thr Lys Val Cys Gly Ala Pro Pro Cys Val Ile Gly Gly
225                 230                 235                 240

Ala Gly Asn Asn Thr Leu His Cys Pro Thr Asp Cys Phe Arg Lys His
                245                 250                 255

Pro Asp Ala Thr Tyr Ser Arg Cys Gly Ser Gly Pro Trp Ile Thr Pro
            260                 265                 270

Arg Cys Leu Val Asp Tyr Pro Tyr Arg Leu Trp His Tyr Pro Cys Thr
            275                 280                 285

Ile Asn Tyr Thr Ile Phe Lys Ile Arg Met Tyr Val Gly Gly Val Glu
            290                 295                 300

His Arg Leu Glu Ala Ala Cys Asn Trp Thr Arg Gly Glu Arg Cys Asp
305                 310                 315                 320

Leu Glu Asp Arg Asp Arg Ser Glu Leu Ser Pro Leu Leu Leu Thr Thr
                325                 330                 335

Thr Gln Trp Gln Val Leu Pro Cys Ser Phe Thr Thr Leu Pro Ala Leu
            340                 345                 350

Ser Thr Gly Leu Ile His Leu His Gln Asn Ile Val Asp Val Gln Tyr
            355                 360                 365
```

```
Leu Tyr Gly Val Gly Ser Ser Ile Ala Ser Trp Ala Ile Lys Trp Glu
    370                 375                 380

Tyr Val Val Leu Leu Phe Leu Leu Leu Ala Asp Ala Arg Val Cys Ser
385                 390                 395                 400

Cys Leu Trp
```

(2) INFORMATION FOR SEQ ID NO:40:

(i) SEQUENCE CHARACTERISTICS:
        (A) LENGTH: 180 amino acids
        (B) TYPE: amino acid
        (D) TOPOLOGY: linear (ii) MOLECULE TYPE: peptide (xi) SEQUENCE DESCRIPTION: SEQ ID NO:40:

```
Met Ala Gln Leu Leu Arg Ile Pro Gln Ala Ile Leu Asp Met Ile Ala
1               5                   10                  15

Gly Ala His Trp Gly Val Leu Ala Gly Ile Ala Tyr Phe Ser Met Val
                20                  25                  30

Gly Asn Trp Ala Lys Val Leu Val Val Leu Leu Leu Phe Ala Gly Val
            35                  40                  45

Asp Ala Glu Thr Ile Val Ser Gly Gly Gln Ala Ala Arg Ala Met Ser
50                  55                  60

Gly Leu Val Ser Leu Phe Thr Pro Gly Ala Lys Gln Asn Ile Gln Leu
65                  70                  75                  80

Ile Asn Thr Asn Gly Ser Trp His Ile Asn Ser Thr Ala Leu Asn Cys
                85                  90                  95

Asn Glu Ser Leu Asn Thr Gly Trp Leu Ala Gly Leu Ile Tyr Gln His
                100                 105                 110

Lys Phe Asn Ser Ser Gly Cys Pro Glu Arg Leu Ala Ser Cys Arg Arg
            115                 120                 125

Leu Thr Asp Phe Asp Gln Gly Trp Gly Pro Ile Ser His Ala Asn Gly
130                 135                 140

Ser Ala Pro Asp Gln Arg Pro Tyr Cys Trp His Tyr Pro Pro Lys Pro
145                 150                 155                 160

Cys Gly Ile Val Pro Ala Lys Ser Val Cys Gly Pro Val Tyr Cys Phe
                165                 170                 175

Thr Pro Ser Pro
            180
```

(2) INFORMATION FOR SEQ ID NO:41:

(i) SEQUENCE CHARACTERISTICS:
        (A) LENGTH: 180 amino acids
        (B) TYPE: amino acid
        (D) TOPOLOGY: linear (ii) MOLECULE TYPE: peptide (xi) SEQUENCE DESCRIPTION: SEQ ID NO:41:

```
Val Ser Gln Leu Leu Arg Ile Pro Gln Ala Val Val Asp Met Val Ala
1               5                   10                  15

Gly Ala His Trp Gly Val Leu Ala Gly Leu Ala Tyr Tyr Ser Met Val
                20                  25                  30

Gly Asn Trp Ala Lys Val Leu Ile Val Ala Leu Leu Phe Ala Gly Val
            35                  40                  45

Asp Gly Glu Thr Tyr Thr Ser Gly Gly Ala Ala Ser His Thr Thr Ser
50                  55                  60
```

```
Thr Leu Ala Ser Leu Phe Ser Pro Gly Ala Ser Gln Arg Ile Gln Leu
 65                  70                  75                  80

Val Asn Thr Asn Gly Ser Trp His Ile Asn Arg Thr Ala Leu Asn Cys
                 85                  90                  95

Asn Asp Ser Leu His Thr Gly Phe Leu Ala Ala Leu Phe Tyr Thr His
            100                 105                 110

Arg Phe Asn Ser Ser Gly Cys Pro Glu Arg Met Ala Ser Cys Arg Pro
            115                 120                 125

Ile Asp Trp Phe Ala Gln Gly Trp Gly Pro Ile Thr Tyr Thr Glu Pro
        130                 135                 140

Asp Ser Pro Asp Gln Arg Pro Tyr Cys Trp His Tyr Ala Pro Arg Pro
145                 150                 155                 160

Cys Gly Ile Val Pro Ala Ser Gln Val Cys Gly Pro Val Tyr Cys Phe
                165                 170                 175

Thr Pro Ser Pro
            180

(2) INFORMATION FOR SEQ ID NO:42:

(i) SEQUENCE CHARACTERISTICS:
        (A) LENGTH: 108 amino acids
        (B) TYPE: amino acid
        (D) TOPOLOGY: linear (ii) MOLECULE TYPE: peptide (xi) SEQUENCE DESCRIPTION: SEQ ID NO:42:

Val Ser Gln Leu Leu Arg Ile Pro Gln Ala Val Met Asp Met Val Ala
  1               5                  10                  15

Gly Ala His Trp Gly Val Leu Ala Gly Leu Ala Tyr Tyr Ser Met Val
                 20                  25                  30

Gly Asn Trp Ala Lys Val Leu Ile Val Met Leu Leu Phe Ala Gly Val
             35                  40                  45

Asp Gly His Thr Arg Val Thr Gly Gly Val Gln Gly His Val Thr Ser
 50                  55                  60

Thr Leu Thr Ser Leu Phe Arg Pro Gly Ala Ser Gln Lys Ile Gln Leu
 65                  70                  75                  80

Val Asn Thr Asn Gly Ser Trp His Ile Asn Arg Thr Ala Leu Asn Cys
                 85                  90                  95

Asn Asp Ser Leu Gln Thr Gly Phe Leu Ala Ala Leu
            100                 105

(2) INFORMATION FOR SEQ ID NO:43:

(i) SEQUENCE CHARACTERISTICS:
        (A) LENGTH: 943 base pairs
        (B) TYPE: nucleic acid
        (C) STRANDEDNESS: single
        (D) TOPOLOGY: linear (ii) MOLECULE TYPE: Other
        (A) DESCRIPTION: cDNA to genomic RNA (xi) SEQUENCE DESCRIPTION: SEQ ID NO:43:

ACAATACGTG TGTCACCCAG ACAGTCGATT TCAGCCTTGA CCCTACCTTC ACCATTGAGA     60

CAATCACGCT CCCCCAGGAT GCTGTCTCCC GCACTCAACG TCGGGGCAGG ACTGGCAGGG    120

GGAAGCCAGG CATCTACAGA TTTGTGGCAC CGGGGGAGCG CCCCTCCGGC ATGTTCGACT    180

CGTCCGTCCT CTGTGAGTGC TATGACGCAG GCTGTGCTTG GTATGAGCTC ACGCCCGCCG    240

AGACTACAGT TAGGCTACGA GCGTACATGA ACACCCCGGG GCTTCCCGTG TGCCAGGACC    300
```

| | | |
|---|---|---|
| ATCTTGAATT TTGGGAGGGC GTCTTTACAG GCCTCACTCA TATAGATGCC CACTTTCTAT | 360 | |
| CCCAGACAAA GCAGAGTGGG GAGAACCTTC CTTACCTGGT AGCGTACCAA GCCACCGTGT | 420 | |
| GCGCTAGGGC TCAAGCCCCT CCCCCATCGT GGGACCAGAT GTGGAAGTGT TTGATTCGCC | 480 | |
| TCAAGCCCAC CCTCCATGGG CCAACACCCC TGCTATACAG ACTGGGCGCT GTTCAGAATG | 540 | |
| AAATCACCCT GACGCACCCA GTCACCAAAT ACATCATGAC ATGCATGTCG GCCGACCTGG | 600 | |
| AGGTCGTCAC GAGCACCTGG GTGCTCGTTG GCGGCGTCCT GGCTGCTTTG GCCGCGTATT | 660 | |
| GCCTGTCAAC AGGCTGCGTG GTCATAGTGG GCAGGGTCGT CTTGTCCGGG AAGCCGGCAA | 720 | |
| TCATACCTGA CAGGGAAGTC CTCTACCGAG AGTTCGATGA GATGGAAGAG TGCTCTCAGC | 780 | |
| ACTTACCGTA CATCGAGCAA GGGATGATGC TCGCCGAGCA GTTCAAGCAG AAGGCCCTCG | 840 | |
| GCCTCCTGCA GACCGCGTCC CGTCAGGCAG AGGTTATCGC CCCTGCTGTC CAGACCAACT | 900 | |
| GGCAAAAACT CGAGACCTTC TGGGCGAAGC ATATGTGGAA CTT | 943 | |

(2) INFORMATION FOR SEQ ID NO:44:

(i) SEQUENCE CHARACTERISTICS:
        (A) LENGTH: 569 base pairs
        (B) TYPE: nucleic acid
        (C) STRANDEDNESS: single
        (D) TOPOLOGY: linear (ii) MOLECULE TYPE: Other
        (A) DESCRIPTION: cDNA to genomic RNA (xi) SEQUENCE DESCRIPTION: SEQ ID NO:44:

| | |
|---|---|
| GTAACACATG TGTCACTCAG ACGGTCGATT TCAGCTTGGA TCCCACTCTC ACCATCGAGA | 60 |
| CGACGACCGT GCCCCAAGAT GCGGTTTCGC GCACGCAGCG GCGAGGTAGG ACTGGCAGGG | 120 |
| GCAGGAGAGG CATCTATAGG TTTGTGACTC CAGGAGAACG GCCCTCGGCG ATGTTCGATT | 180 |
| CTTCGGTCCT ATGTGAGTGT TATGACGCGG GCTGTGCTTG GTATGAGCTC ACGCCCGCTG | 240 |
| AGACCTCGGT TAGGTTGCGG GCTTACCTAA ATACACCAGG GTTGCCCGTC TGCCAGGACC | 300 |
| ATCTGGAGTT CTGGGAGAGC GTCTTCACAG GCCTCACCCA CATAGACGCC CACTTCTTGT | 360 |
| CCCAGACTAA GCAGGCAGGA GACAACTTCC CCTACCTGGT AGCATACCAA GCCACAGTGT | 420 |
| GCGCCAGGGC TAAGGCTCCA CCTCCATCGT GGGATCAAAT GTGGAAGTGT CTCATACGGC | 480 |
| TAAAGCCTAC GCTGCACGGG CCAACGCCCC TGCTGTATAG GCTAGGAGCC GTCCAGAATG | 540 |
| AGGTCACCCT CACACACCCT ATAACCAAA | 569 |

(2) INFORMATION FOR SEQ ID NO:45:

(i) SEQUENCE CHARACTERISTICS:
        (A) LENGTH: 313 amino acids
        (B) TYPE: amino acid
        (D) TOPOLOGY: linear (ii) MOLECULE TYPE: peptide (xi) SEQUENCE DESCRIPTION: SEQ ID NO:45:

Asn Thr Cys Val Thr Gln Thr Val Asp Phe Ser Leu Asp Pro Thr Phe
1               5                   10                  15

Thr Ile Glu Thr Ile Thr Leu Pro Gln Asp Ala Val Ser Arg Thr Gln
            20                  25                  30

Arg Arg Gly Arg Thr Gly Arg Gly Lys Pro Gly Ile Tyr Arg Phe Val
        35                  40                  45

Ala Pro Gly Glu Arg Pro Ser Gly Met Phe Asp Ser Ser Val Leu Cys
    50                  55                  60

```
Glu Cys Tyr Asp Ala Gly Cys Ala Trp Tyr Glu Leu Thr Pro Ala Glu
 65                  70                  75                  80

Thr Thr Val Arg Leu Arg Ala Tyr Met Asn Thr Pro Gly Leu Pro Val
                 85                  90                  95

Cys Gln Asp His Leu Glu Phe Trp Glu Gly Val Phe Thr Gly Leu Thr
            100                 105                 110

His Ile Asp Ala His Phe Leu Ser Gln Thr Lys Gln Ser Gly Glu Asn
            115                 120                 125

Leu Pro Tyr Leu Val Ala Tyr Gln Ala Thr Val Cys Ala Arg Ala Gln
130                 135                 140

Ala Pro Pro Ser Trp Asp Gln Met Trp Lys Cys Leu Ile Arg Leu
145                 150                 155                 160

Lys Pro Thr Leu His Gly Pro Thr Pro Leu Leu Tyr Arg Leu Gly Ala
                165                 170                 175

Val Gln Asn Glu Ile Thr Leu Thr His Pro Val Thr Lys Tyr Ile Met
            180                 185                 190

Thr Cys Met Ser Ala Asp Leu Glu Val Val Thr Ser Thr Trp Val Leu
            195                 200                 205

Val Gly Gly Val Leu Ala Ala Leu Ala Ala Tyr Cys Leu Ser Thr Gly
210                 215                 220

Cys Val Val Ile Val Gly Arg Val Val Leu Ser Gly Lys Pro Ala Ile
225                 230                 235                 240

Ile Pro Asp Arg Glu Val Leu Tyr Arg Glu Phe Asp Glu Met Glu Glu
                245                 250                 255

Cys Ser Gln His Leu Pro Tyr Ile Glu Gln Gly Met Met Leu Ala Glu
            260                 265                 270

Gln Phe Lys Gln Lys Ala Leu Gly Leu Leu Gln Thr Ala Ser Arg Gln
            275                 280                 285

Ala Glu Val Ile Ala Pro Ala Val Glu Thr Asn Trp Gln Lys Leu Glu
            290                 295                 300

Thr Phe Trp Ala Lys His Met Trp Asn
305                 310

(2) INFORMATION FOR SEQ ID NO:46:

(i) SEQUENCE CHARACTERISTICS:
        (A) LENGTH: 189 amino acids
        (B) TYPE: amino acid
        (D) TOPOLOGY: linear (ii) MOLECULE TYPE: peptide (xi) SEQUENCE DESCRIPTION: SEQ ID NO:46:

Asn Thr Cys Val Thr Gln Thr Val Asp Phe Ser Leu Asp Pro Thr Leu
 1               5                  10                  15

Thr Ile Glu Thr Thr Thr Val Pro Gln Asp Ala Val Ser Arg Thr Gln
                20                  25                  30

Arg Arg Gly Arg Thr Gly Arg Gly Arg Arg Gly Ile Tyr Arg Phe Val
            35                  40                  45

Thr Pro Gly Glu Arg Pro Ser Ala Met Phe Asp Ser Ser Val Leu Cys
 50                 55                  60

Glu Cys Tyr Asp Ala Gly Cys Ala Trp Tyr Glu Leu Thr Pro Ala Glu
 65                 70                  75                  80

Thr Ser Val Arg Leu Arg Ala Tyr Leu Asn Thr Pro Gly Leu Pro Val
                85                  90                  95

Cys Gln Asp His Leu Glu Phe Trp Glu Ser Val Phe Thr Gly Leu Thr
```

-continued

|   |   |   |   |   |   |   | 100 |   |   |   |   | 105 |   |   |   |   | 110 |   |   |
|---|---|---|---|---|---|---|---|---|---|---|---|---|---|---|---|---|---|---|---|
| His | Ile | Asp | Ala | His | Phe | Leu | Ser | Gln | Thr | Lys | Gln | Ala | Gly | Asp | Asn |
|   |   |   |   | 115 |   |   |   |   | 120 |   |   |   |   | 125 |   |
| Phe | Pro | Tyr | Leu | Val | Ala | Tyr | Gln | Ala | Thr | Val | Cys | Ala | Arg | Ala | Lys |
|   |   | 130 |   |   |   |   | 135 |   |   |   | 140 |   |   |   |   |
| Ala | Pro | Pro | Ser | Trp | Asp | Gln | Met | Trp | Lys | Cys | Leu | Ile | Arg | Leu |
| 145 |   |   |   |   | 150 |   |   |   | 155 |   |   |   |   | 160 |
| Lys | Pro | Thr | Leu | His | Gly | Pro | Thr | Pro | Leu | Leu | Tyr | Arg | Leu | Gly | Ala |
|   |   |   |   | 165 |   |   |   |   | 170 |   |   |   |   | 175 |   |
| Val | Gln | Asn | Glu | Val | Thr | Leu | Thr | His | Pro | Ile | Thr | Lys |
|   |   |   | 180 |   |   |   |   | 185 |   |   |   |   |

NUCLEOTIDE AND PEPTIDE SEQUENCES OF A HEPATITIS C VIRUS ISOLATE, DIAGNOSTIC AND THERAPEUTIC APPLICATIONS

This is a division of application Ser. No. 07/965,285, filed Mar. 18, 1993.

The present invention relates to nucleotide and peptide sequences of a European, more particularly French, strain of the hepatitis C virus, as well as to the diagnostic and therapeutic applications of these sequences.

The hepatitis C virus is a major causative agent of infections by viruses previously called "Non-A Non-B" viruses. Infections by the C virus in fact now represent the most frequent forms of acute hepatitides and chronic Non-A Non-B hepatitides (Alter et al. (1), Choo et al., (3); Hopf et al., (5); Kuo et al., (8); Miyamura et al., (11). Furthermore, there is a relationship (the significance of which is still poorly understood) between the presence of anti-HCV antibodies and the development of primary liver cancers. It has also been shown that the hepatitis C virus is involved in both chronic or acute Non-A Non-B hepatitides linked to transfusions of blood products or of sporadic origin.

The genome of the hepatitis C virus has been cloned and the nucleotide sequence of an American isolate has been described in EP-A-0 318 216, EP-A-0 363 025, EP-A-0 388 232 and WO-A-90/14436. Moreover, data is currently available on the nucleotide sequences of several Japanese isolates relating both to the structural region and the nonstructural region of the virus (Okamoto et al., (12), Enomoto et al., (4), Kato et al., (6); Takeuchi et al., (15 and 16)). The virus exhibits some similarities with the group comprising Flavi- and Pestiviruses; however, it appears to form a distinct class, different from viruses known up until now (Miller and Purcell, (10)).

In spite of the breakthrough which the cloning of HCV represented, several problems persist:

a substantial genetic variability exists in certain regions of the virus which has made it possible to describe the existence of two groups of viruses, diagnosis of the viral infection remains difficult in spite of the possibility of detecting anti-HCV antibodies in the serum of patients. This is due to the existence of false positive results and to a delayed seroconversion following acute infection. Finally there are clearly cases where only the detection of the virus RNA makes it possible to detect the HCV infection while the serology remains negative.

These problems have important implications both with respect to diagnosis and protection against the virus.

The authors of the present invention have carried out the cloning and obtained the partial nucleotide sequence of a French isolate of HCV (called hereinafter HCV E1) from a blood donor who transmitted an active chronic hepatitis to a recipient. Comparison of the nucleotide sequences and the peptide sequences obtained with the respective sequences of the American and Japanese isolates showed that there was
a high conservation of nucleic acids in the noncoding region of HCV E1,
a high genetic variability in the structural regions called E1 and E2/NS1,
a smaller genetic variability in the nonstructural region.

The present invention is based on new nucleotide and polypeptide sequences of the hepatitis C virus which have not been described in the abovementioned state of the art.

The subject of the present invention is thus a DNA sequence of HCV E1 comprising a DNA sequence chosen from the nucleotide sequences of at least 10 nucleotides between the following nucleotides (n); $n_{118}$ to $n_{138}$; $n_{177}$ to $n_{202}$; $n_{233}$ to $n_{247}$; $n_{254}$ to $n_{272}$ and $n_{272}$ to $n_{288}$ represented in the sequence SEQ ID NO.2, and, $n_{156}$ to $n_{170}$; $n_{170}$ to $n_{217}$; $n_{287}$ to $n_{283}$ and $n_{3/0}$ to $n_{334}$ represented in the sequence SEQ ID NO.4; as well as analogous nucleotide sequences resulting from degeneracy of the genetic code.

The subject of the invention is in particular the following nucleotide sequences: SEQ ID NO.2, SEQ ID NO.4 and SEQ ID NO.6.

The oligonucleotide sequences may be advantageously synthesised by the Applied Bio System technique.

The subject of the invention is also a peptide sequence of HCV E1 comprising a peptide sequence chosen from the sequences of at least 7 amino acids between the following amino acids (aa): $aa_{58}$ to $aa_{66}$; $aa_{78}$ to $aa_{101}$ represented in the peptide sequence SEQ ID NO.3; $aa_{49}$ to $aa_{78}$; $aa_{98}$ to $aa_{111}$; $aa_{123}$ to $aa_{133}$; $aa_{140}$ to $aa_{149}$ represented in the peptide sequence SEQ ID NO.5; as well as homologous peptide sequences which do not induce modification of biological and immunological properties.

Preferably, the peptide sequence is chosen from the following amino acid sequences: $aa_{58}$ to $aa_{66}$; $aa_{76}$ to $aa_{101}$ represented in the peptide sequence SEQ ID NO.3, $aa_{49}$ to $aa_{78}$; $aa_{98}$ to $aa_{111}$; $aa_{123}$ to $aa_{133}$ and $aa_{140}$ to $aa_{149}$ represented in the peptide sequence SEQ ID NO.5.

Moreover, the peptide sequence is advantageously chosen from the peptide sequences SEQ ID NO.3, SEQ ID NO.5 and SEQ ID NO.7.

The subject of the invention is also a nucleotide sequence encoding a peptide sequence as defined above.

Moreover, the subject of the invention is a polynucleotide probe comprising a DNA sequence as defined above.

The subject of the invention is also an immunogenic peptide comprising a peptide sequence as defined above.

The peptide sequences according to the invention can be obtained by conventional methods of synthesis or by the application of genetic engineering techniques comprising the insertion of a DNA sequence, encoding a peptide sequence according to the invention, into an expression vector such as a plasmid and the transformation of cells using this expression vector and the culture of these cells.

The subject of the invention is also plasmids or expression vectors comprising a DNA sequence encoding a peptide sequence as defined above as well as hosts transformed using this vector.

The preferred plasmids are those deposited with CNCM on Jun. 5, 1991 under the numbers I-1105, I-1106 and I-1107.

The subject of the invention is also monoclonal antibodies directed against a peptide sequence according to the invention or an immunogenic sequence of such a polypeptide.

The monoclonal antibodies according to the invention can be prepared according to a conventional technique. For this purpose, the polypeptides may be coupled, if necessary, to an immunogenic agent such as tetanus anatoxin using a coupling agent such as glutaraldehyde, a carbodiimide or a bisdiazotised benzidine.

The present invention also encompasses the fragments and the derivatives of monoclonal antibodies according to the invention. These fragments are especially F(ab')$_2$ fragments which can be obtained by enzymatic cleavage of the antibody molecules with pepsin, the Fab' fragments which can be obtained by reducing the disulphide bridges of the F(ab')$_2$ fragments, and the Fab fragments which can be obtained by enzymatic cleavage of the antibody molecules with papain in the presence of a reducing agent. These fragments, as well as the Fc fragments, can also be obtained by genetic engineering.

The derivatives of monoclonal antibodies are for example antibodies or fragments of these antibodies to which markers, such as a radioisotopes, are attached. The derivatives of monoclonal antibodies are also antibodies or fragments of these antibodies to which therapeutically active molecules are attached.

The subject of the invention is also an analytical kit for the detection of nucleotide sequences specific to the HVC E1 strain, comprising one or more probes as defined above.

The subject of the present invention is also an in vitro diagnostic process involving the detection of antigens specific to HCV E1, in a biological sample possibly containing the said antigens, in which, the biological sample is exposed to an antibody or an antibody fragment, as defined above; as well as a diagnostic kit for carrying out the process.

The subject of the invention is also an in vitro diagnostic process involving the detection of antibodies specific to HCV E1 in a biological sample possibly containing the said antibodies, in which a biological sample is exposed to an antigen containing an epitope corresponding to a peptide sequence, as well as a diagnostic kit for the detection of specific antibodies, comprising an antigen containing an epitope corresponding to a peptide sequence as defined above.

These procedures may be based on a radioimmunological method of the RIA, RIPA or IRMA type or an immunoenzymatic method of the WESTERN-BLOT type carried out on strips or of the ELISA type.

The subject of the invention is also a therapeutic composition comprising monoclonal antibodies or fragments of monoclonal antibodies or derivatives of monoclonal antibodies as defined above.

Advantageously, the monoclonal antibody derivatives are monoclonal antibodies or fragments of these antibodies attached to a therapeutically active molecule.

The subject of the invention is also an immunogenic composition containing an immunogenic sequence as defined above, optionally attached to a carrier protein, the said immunogenic sequence being capable of inducing protective antibodies or cytotoxic T lymphocytes. Anatoxins such as tetanus anatoxin may be used as carrier protein. Alternatively, immunogens produced according to the MAP (Multiple Antigenic Peptide) technique may also be used.

In addition to the immunogenic peptide sequence, the immunogenic composition may contain an adjuvant possessing immunostimulant properties.

The following are among the adjuvants which may be used: inorganic salts such as aluminium hydroxide, hydrophobic compounds or surface-active agents such as incomplete Freund's adjuvant, squalene or liposomes, synthetic polynucleotides, microorganisms or microbial components such as murabutide, synthetic artificial molecules such as imuthiol or levamisole, or alternatively cytokines such as interferons α, β, γ or interleukins.

The subject of the invention is also a process for assaying a peptide sequence as defined above, comprising the use of monoclonal antibodies directed against this peptide sequence.

The subject of the invention is also a process for preparing a peptide sequence as defined above, comprising the insertion of a DNA sequence, encoding the peptide sequence, into an expression vector, the transformation of cells using this expression vector and the culture of the cells.

The production of the DNA of the sequences of the HCV E1 strain will be described below in greater detail with reference to the accompanying figures in which:

FIG. 1 represents the location of the amplified and sequenced HCV E1 regions;

FIG. 2 represents the comparison of the nucleotide sequence of HCV E1 (1) [SEQ ID NO:1], in the non-coding region, with the sequences of an American isolate (2) [SEQ ID NO:24] and two Japanese isolates: HCJ1 (3) [SEQ ID NO:25] and HCJ4 (4) [SEQ ID NO:26] respectively described in WO-A-90/14436 and by Okamoto et al. (12);

FIG. 3 represents the comparison of the nucleotide sequence of HCV E1 (1) [SEQ ID NO:3], in the region E1, with the sequences of an American isolate (HCVpt) (2) [SEQ ID NO:27] described in WO 90/14436 and three Japanese isolates: HCVJ-1 (3) [SEQ ID NO:28], SCJ1 (4) [SEQ ID NO:29] and HCJ4 (5) [SEQ ID NO:30] described in Takeuchi et al. (15); Okamoto et al. (12);

FIG. 4 represents the comparison of the aminoacid sequence, in the region E1, of HCV E1 (1) [SEQ ID NO:3] with the American isolate HCVpt (2) [SEQ ID NO:31] and the Japanese isolates: HCVJ1 (3) [SEQ ID NO:32], HCJ1 (4) [SEQ ID NO:33] and HCJ4 (5) [SEQ ID NO:34]; the variable regions are boxed;

FIG. 5 represents the comparison of the nucleotide sequence, in the region E2/NS1, of HCV E1 (1) [SEQ ID NO:4] with the American isolate HCVpt (2) [SEQ ID NO:35] described in WO-A-90/14436 and the Japanese isolates HCJ1 (3) [SEQ ID NO:36], HCJ4 (4) [SEQ ID NO:37] and HCVJ1 (5) [SEQ ID NO:38] described by Okamoto et al. (12); Takeuchi et al. (15);

FIG. 6 represents a comparison of the aminoacid sequence, in the region E2/NS1, of HCV E1 (1) [SEQ ID NO:5] with the American isolate HCVpt (2) [SEQ ID NO:39] and the Japanese isolates HCJ1 (3) [SEQ ID NO:40], HCJ4 (4) [SEQ ID NO:41] and HCVJ1 (5) [SEQ ID NO:47]; the variable regions are boxed;

FIG. 7 represents the hydrophilicity profile of HCV E1 in the region E2/NS1; the hydrophobic regions are located under the middle line;

FIG. 8 represents the comparison of the nucleotide sequence, in the region NS3/NS4, of HCV E1 (1) [SEQ ID NO:6] with the American isolate HCVpt (2) [SEQ ID NO:43] described in WO-A-90/14436 and the Japanese isolate HCVJ1 (3) [SEQ ID NO:44] described by Kubo et al. (7);

FIG. 9 represents the comparison of the aminoacid sequence, in the region NS3/NS4, of HCV E1 (1) [SEQ ID NO:2] with the American isolate HCVpt (2) [SEQ ID NO:45] and the Japanese isolate HCVJ1 (3) [SEQ ID NO:46].

I—Preparation of the nucleotide sequences

1) Preparation of the HCV E1 RNA

The HCV E1 RNA was prepared as previously described in EP-A-O,318,216 from the serum of a French blood donor suffering from a chronic hepatitis, anti-HCV positive (anti-C100) (Kubo et al. (7)).

100 μl of serum were diluted in a final volume of 1 ml, in the following extraction buffer: 50 mM tris-HCl, pH.8, 1 mM EDTA, 100 mM NaCl, 1 mg/ml of proteinase K, and 0.5% SDS. After digestion with proteinase K for 1 h at 37° C., the proteins were extracted with one volume of TE-saturated phenol (10 mM Tris-HCl, pH.8, 1 mM EDTA). The aqueous phase was then extracted twice with one volume of phenol/chloroform (1:1) and once with one volume of chloroform. The aqueous phase was then adjusted to a final concentration of 0.2 M sodium acetate and the nucleic acids were precipitated by the addition of two volumes of ethanol. After centrifugation, the nucleic acids were suspended in 30 μl of DEPC-treated sterile distilled water.

2) Reverse transcription and amplification A complementary DNA (cDNA) was synthesised using as primer either oligonucleotides specific to HCV, represented in Table I below, or a mixture of hexanucleotides not specific to HCV, and murine reverse transcriptase. A PCR (Polymerase Chain Reaction) was carried out over 40 cycles at the following temperatures: 94° C. (1 min), 55° C. (1 min), 72° C. (1 min), on the cDNA thus obtained, using pairs of primers specific to HCV (Table I below). Various HCV primers were made from the sequence of HCV prototype (HCVpt), isolated from a chronically infected chimpanzee (Bradley et al. (2); Alter et al. (1), EP-A-0,318,216). The nucleotide sequence of the 5' region of the E2/NS1 gene was obtained using a strategy derived from the sequence-independent single primer amplification technique (SISPA) described by Reyes et al. (13). It consists in ligating double-stranded adaptors to the ends of the DNA synthesised using an HCV-specific primer localised in 5' of the HCVpt sequence (primer NS1A in Table I). A semi-specific amplification is then carried out using an HCV-specific primer as well as a primer corresponding to the adaptor. This approach makes it possible to obtain amplification products spanning the 5' region of the primer used for the synthesis of the cDNA.

sequence of the inserts was determined by the dideoxynucleotide-based method described by Sanger et al., (14).

II—Study of the nucleotide sequences of the French isolate (HCV E1)

The location of the various amplification products which made it possible to obtain the nucleotide sequence of the HCV E1 isolate in nonstructural and structural regions as well as in the noncoding region of the virus, is schematically represented in FIG. 1.

1) Nucleotide sequence of HCV E1 in the noncoding 5' region

The amplified and sequenced noncoding 5' region of HCV E1 is called ID SEQ No.1. It corresponds to a 256-base pair (bp) fragment located in position −259 to −4 in HCVpt as described in WO-A-90/14436. Comparison of the HCV E1 sequence with those previously published shows a very high nucleic acid conservation (FIG. 2).

2) Nucleotide and peptide sequences of HCV E1 in the structural region

The nucleotide sequences probably correspond to two regions encoding the virus envelope proteins (currently designated as the E1 and E2/NS1 regions).

For the E1 region, the sequence obtained for HCV E1 corresponds to the 3' moiety of the gene. It has been called

TABLE I

Sequence of the primers and probes.

a) Primers[a]:

| | | | |
|---|---|---|---|
| NS3 | (+) | 5'ACAATACGTGTGTCACC (3013-3029) | [SEQ ID NO:8] |
| NS4 | (−) | 5'AAGTTCCACATATGCTTCGC (3955-3935) | [SEQ ID NO:9] |
| NS1A | (−) | 5'TCCGTTGGCATAACTGATAG (83-64) | [SEQ ID NO:10] |
| NS1B | (+) | 5'CTATCAGTTATGCCAACGGA (64-83) | [SEQ ID NO:11] |
| NS1C | (−) | 5'GTTGCCCGCCCCTCCGATGT (380-361) | [SEQ ID NO:12] |
| NS1D | (+) | 5'CCCAGCCCCGTGGTGGTGGG (183-202) | [SEQ ID NO:13] |
| NS1E | (−) | 5'CCACAAGCAGGAGCAGACGC (860-841) | [SEQ ID NO:14] |
| NCA | (+) | 5'CCATGGCGTTAGTATGAGT (−259- −239) | [SEQ ID NO:15] |
| NCB | (−) | 5'GCAGGTCTACGAGACCTC (−4- −23) | [SEQ ID NO:16] |
| E1A | (+) | 5'TTCTGGAAGACGGCGTGAAC (470-489) | [SEQ ID NO:17] |
| E1B | (−) | 5'TCATCATATCCCATGCCATG (973-954) | [SEQ ID NO:18] | b) probes[a]:

| | | | |
|---|---|---|---|
| NS3/NS4 | (+) | 5'CCTTCACCATTGAGACAATCACGCTCCCCCAGGATGCTGT (3058-3097) | [SEQ ID NO:19] |
| NS1 | (+) | 5'CTGTCCTGAGAGGCTAGCCAGCTGCCGACCCCTTACCGAT (5-44) | [SEQ ID NO:20] |
| NS1B/C | (+) | 5'AGGTCGGGCGCGCCCACCTACAGCTGGGGTGAAAATGATA (210-248) | [SEQ ID NO:21] |
| NC | (+) | 5'GTGCAGCCTCCAGGACCCCC ( 235- −216) | [SEQ ID NO:22] |
| E1 | (−) | 5'CTCGTACACAATACTCGAGT (646-627) | [SEQ ID NO:23] | a. The nucleotide sequences and their locations correspond to the HCV prototype (HCVpt) (EP-A-0,318,216 and WO-A-90/14436).

3) Cloning and sequencing

The amplification products were cloned into M13 mp19 or into the bacteriophage lambda gt 10 as described by Thiers et al. (17). The probes used for screening the DNA sequences are represented in Table I above. The nucleotide ID SEQ No.2. This 501-bp sequence is located in position 470 and 973 in the HCVpt sequence as described in WO-A-90/14436. Comparison of this sequence with those previously described shows a high genetic variability (FIG. 3). Indeed, depending on the isolates studied, a difference of 10 to 27% in nucleic acid composition and 7 to 20% in amino acid composition may be observed as shown in Table II below. Furthermore, comparison of the peptide sequence reveals the existence of two hypervariable regions which are boxed in FIG. 4.

Figure 7:
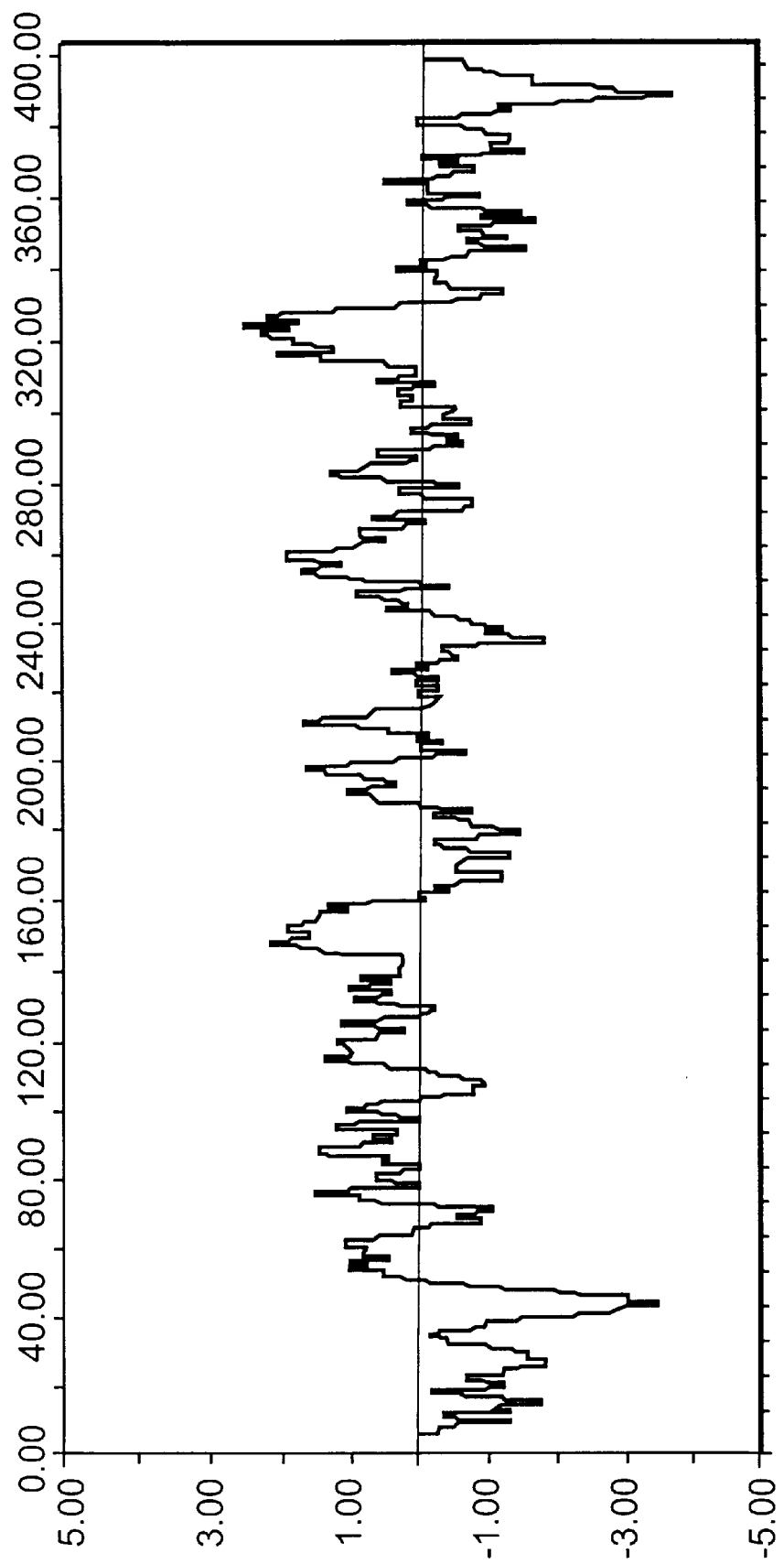

For the E2/NS1 region, the HVC E1 sequence data were obtained from three overlapping amplification products (FIG. 1). The consensus sequence thus obtained (1210 bp) contains the entire E2/NS1 gene and was called ID SEQ No.3. The sequence of the E2/NS1 region of HCV E1 is situated in position 999 and 2209 compared with the HCVpt sequence described in WO-A-90/14436. Comparison of the HCV E1 sequences with the isolates previously described shows a difference of 13 to 33% in the case of nucleic acids and 11 to 30% in the case of amino acids (FIG. 5 and 6, Table II). The highest variability is observed in 5' of the E2/NS1 gene (FIG. 5). Comparison of amino acids shows the existence of four hypervariable regions which are boxed in FIG. 6. The hydrophilicity profile of the E2/NS1 region (Kyte and Dolittle, (9)) is given in FIG. 7. A hydrophilic region flanked by two hydrophobic regions are observed. Both hydrophobic regions probably correspond to the signal sequence as well as to the transmembrane segment. Finally, the central region has ten potential glycolisation [sic] sites (N-X-T/S), which are conserved in the various isolates (FIG. 6).

3) Nucelotide and peptide sequence of HCV E1 in the nonstructural region

The sequence data for HCV E1 in the nonstructural region correspond to the 3' and 5' terminal parts of the NS3 and NS4 genes respectively (FIG. 1). The sequence obtained for HCV E1 (943 bp) is located in position 4361 to 5303 in the HCVpt sequence and was called ID SEQ No.4. The sequence homology is 95% with the HCVpt isolate and 78.6% with a Japanese isolate (FIG. 8, Table II above). In the case of the comparison of amino acids, a homology of 98% and 93% was observed with the HCVpt and Japanese isolates respectively (FIG. 8, Table II above).

Thus, comparison of the nucleotide sequence of the HCV E1 isolate with that of the American and Japanese isolates shows that the French isolate is different from the isolates described above. It reveals the existence of highly variable regions in the envelope proteins. The variability of the nonstructural region studied is lower. Finally, the noncoding 5' region shows a high conservation.

These results have implications both for diagnosis and prevention of HVC.

As far as diagnosis is concerned, definition of the hypervariable regions and of the conserved regions can lead to: the definition of synthetic peptides which allow the expression of epitopes specific to the various HCV groups.

For the envelope protein E1, peptides for the determination of type-specific epitopes are advantageously defined in a region between amino acids 75 to 100 (FIG. 4). Likewise, for the protein E2/NS1, peptides allow [sic] characterisation of specific epitopes are synthesised in regions preferably between amino acids 50 and 149, (FIG. 6).

The expression of all or part of the cloned sequences, in particular clones corresponding to the envelope regions of the virus, make it possible to obtain new antigens for the development of diagnostic reagents and for the production of immunogenic compositions. Finally, the preparation of a substantial part of the nucleotide sequence of this isolate allows the production of the entire length of complementary DNA which can be used for a better understanding of the mechanisms of the viral infection and also for diagnostic and preventive purposes.

TABLE II

Difference in nucleic acids (n.a.) and amino acids (a.a.) between the French isolate (HCV E1) and the American (HCVpt) and japanese (HCVJ1, HCJ1, HCJ4) isolates.

|  |  | HCVpt | HCVJ1 | HCJ1 | HCJ4 |
|---|---|---|---|---|---|
| HCVE1 E1 | n.a. | 10.6 | 27.3 | 10.4 | 26.5 |
|  | a.a. | 7.2 | 19.9 | 8.4 | 20.5 |
| HCVE1 E2/NS1 | n.a. | 12.8% | 33.2% | 14.5% | 29.8% |
|  | a.a. | 12.2% | 29.7% | 15.6% | 26.1% |
| HCVE1 NS3/NS4 | n.a. | 5.2% | 21.4% | — | — |
|  | a.a. | 2.2% | 6.9% | — | — |

REFERENCES

1. Alter, H. J., Purcell, R. H., Shib, J. W., Melpolder, J. C., Houghton, M., Choo, Q. -L. & Kuo, G. (1989). Detection of antibody to hepatitis C virus in prospectively followed transfusion recipients with acute and chronic Non-A, Non-B hepatitis. New England Journal of Medicine 321, 1494–1500.
2. Bradley, D. W., Cook, E. H., Maynard, J. E., McCaustland, K. A., Ebert, J. W., Dolana, G. H., Petzel, R. A., Kantor, R. J., Heilbrunn, A., Fields, H. A. & Murphy, B. L. (1979).
Experimental infection of chimpanzees with antihemophilic (factor VIII) materials: recovery of virus-like particles associated with Non-A, Non-B hepatitis. Journal of Medical Virology 3, 253–269.
3. Choo, Q. -L., Kuo, G., Weiner, A. J., Overby, L. R., Bradley, D. W. & Houghton, M. (1989). Isolation of a cDNA clone derived from a blood-borne Non-A, Non-B viral hepatitis genome. Science 244, 359–362.
4. Enomoto, N., Takada, A., Nakao, T. & Date, T. (1990). There are two major types of hepatitis C virus in Japan. Biochemical and Biophysical Research Communications 170, 1021–1025.
5. Hopf, U., Möller, B., Küther, D., Stemerowicz, R., Lobeck, H., Lüdtke-Handjery, A., Walter, E., Blum, H. E., Roggendorf, M. & Deinhardt, F. (1990). Long-term follow-up of post transfusion and sporadic chronic hepatitis Non-A, Non-B and frequency of circulating antibodies to hepatitis C virus (HCV). Journal of Hepatology 10, 69–76.
6. Kato, N., Hijakata, M., Ootsuyama, Y., Nakagawa, M., Ohkoshi, S., Sugimura, T. & Shimotohno, K. (1990). Molecular cloning of the human hepatitis C virus genome from Japanese patients with Non-A, Non-B hepatitis. Proceedings of the National Academy of Sciences, U.S.A. 87, 9524–9528.
7. Kubo, Y., Takeuchi, K., Boonmar, S., Katayama, T., Choo, Q. -L., Kuo, G., Weiner, A. J., Bradley D. W., Houghton, M., Saito, I. & Miyamura, T. (1989). A cDNA fragment of hepatitis C virus isolated from an implicated donor of post-transfusion Non-A, Non-B hepatitis in Japan. Nucleic Acids Research 17, 10367–10372.
8. Kuo, G., Choo, Q. -L., Alter, H. J., Gitnick, G. L., Redeker, A. G., Purcell, R. H., Miyamura, T., Dienstag, J. L., Alter, M. J., Stevens, C. E., Tegtmeier, G. E., Bonino, F., Colombo, M., Lee, W. S., Kuo, C., Berger, K., Shuster, J. R., Overby, L. R., Bradley, D. W. & Houghton, M. (1989). An assay for circulating antibodies to a major etiologic virus of human Non-A, Non-B hepatitis. Science 244, 362–364.
9. Kyte, W. & Doolittle, R. F. (1982). A simple method for displaying the hydropathic of a protein. Journal of Molecular Biology 157, 105–132.

10. Miller, R. H. & Purcell, R. H. (1990). Hepatitis C virus shares amino acid sequence similarity with pestiviruses and flaviviruses as well as members of two plant virus super groups. Proceedings of the National Academy of Sciences, U.S.A. 87, 2057–2061.
11. Miyamura, T., Saito, T., Katayama, T., Kikuchi, S., Tateda, A., Houghton, M., Choo, Q. -L. & Kuo, G. (1990). Detection of antibody against antigen expressed by molecularly cloned hepatitis C virus cDNA: application to diagnosis and blood screening for posttransfusion hepatitis. Proceedings of the National Academy of Sciences, U.S.A. 87, 983–987.
12. Okamoto, H., Okada, S., Sugiyama, Y., Yotsumoto, S., Tanaka, T., Yoshizawa, H., Tsuda, F., Miyakawa, Y. & Mayumi, M. (1990). The 5' terminal sequence of the hepatitis C virus genome. Japanese Journal of Experimental Medicine 60, 167–177.
13. Reyes, G. R., Purdy, M. A., Kim, J. P., Luk, K. -C., Young, L. M., Fry, K. E. & Bradley, D. W. (1990). Isolation of a cDNA from the virus responsible for enterically transmitted Non-A, Non-B hepatitis. Science 247, 1335–1339.
14. Sanger, F. S., Nicklen, S. & Coulsen, A. R. (1977). DNA sequencing with chain terminating inhibition. Proceedings of the National Academy of Sciences, U.S.A. 74, 5463–5467.
15. Takeuchi, K., Boonmar, S., Kubo, Y., Katayama, T., Harada, H., Ohbayashi, A., Choo, Q., -L., Houghton, M., Saito, I. & Miyamura, T. (1990a). Hepatitis C viral cDNA clones isolated from a healthy carrier donor implicated in post-transfusion Non-A, Non-B hepatitis. Gene 91 (2), 287–291.
16. Takeuchi, K., Kubo, Y., Boonmar, S., Watanabe, Y., Katayama, T., Choo, Q. -L., Kuo, G., Houghton, M., Saito, I. & Miyamura, T. (1990b). Nucleotide sequence of core and envelope genes of the hepatitis C virus genome derived directly from human healthy carriers. Nucleic Acids Research 18, 4626.
17. Thiers, V., Nakajima, E. N., Kremsdorf, D., Mack, D., Schellekens, H., Driss, F., Goude, A., Wands, J., Sninsky, J., Tiollais, P. & Brechot, C. (1988). Transmission of hepatitis B from hepatitis B seronegative subjects. Lancet ii, 1273–1276

Symbols for the amino acids

| | | |
|---|---|---|
| A | Ala | alanine |
| C | Cys | cysteine |
| D | Asp | aspartic acid |
| E | Glu | glutamic acid |
| F | Phe | phenylalanine |
| G | Gly | glycine |
| H | His | histidine |
| I | Ile | isoleucine |
| K | Lys | lysine |
| L | Leu | leucine |
| M | Met | methionine |
| N | Asn | asparagine |
| P | Pro | proline |
| Q | Gln | glutamine |
| R | Arg | arginine |
| S | Ser | serine |
| T | Thr | threonine |
| V | Val | valine |
| W | Trp | tryptophan |
| Y | Tyr | tyrosine |

We claim:

1. Human or murine monoclonal antibodies specific for a peptide sequence of HCV E1, wherein said peptide sequence consists of at least 7 consecutive amino acids selected from the group consisting of:
   (a) $aa_{58}$ to $aa_{66}$ of SEQ ID NO:3;
   (b) $aa_{49}$ to $aa_{78}$ of SEQ ID NO:5; and
   (c) $aa_{123}$ to $aa_{133}$ of SEQ ID NO:5.

2. Human or murine monoclonal antibodies specific for a peptide sequence of HCV E1, wherein said peptide sequence is selected from the group consisting of:
   (a) $aa_{58}$ to $aa_{66}$ of SEQ ID NO:3;
   (b) $aa_{49}$ to $aa_{78}$ of SEQ ID NO:5; and
   (c) $aa_{123}$ to $aa_{133}$ of SEQ ID NO:5.

3. Human or murine monoclonal antibodies directed against a peptide sequence of HCV E1 selected from the group consisting of SEQ ID NO:3, SEQ ID NO:5 and SEQ ID NO:7.

4. Fragments Fab, Fab', F(ab')$_2$, or Fc of the monoclonal antibodies of claims 1, 2, or 3.

5. The monoclonal antibodies of claims 1, 2, or 3, wherein said monoclonal antibodies further comprise markers or therapeutically active molecules attached to said monoclonal antibodies.

6. The fragments of claim 4, wherein said fragments further comprise markers or therapeutically active molecules attached to said fragments.

7. A hybridoma producing the monoclonal antibodies of claims 1, 2 or 3.

8. An in vitro diagnostic method for detecting HCV E1-specific antigens in a biological sample, said process comprising contacting the antibodies of claims 1, 2, or 3 with the biological sample.

9. An in vitro diagnostic method for detecting HCV E1-specific antigens in a biological sample, said process comprising contacting the fragments of claim 4 with the biological sample.

10. A diagnostic kit for detecting HCV E1-specific antigens in a biological sample, said kit comprising:
    (a) the antibodies of claims 1, 2, or 3, wherein said antibodies are labelled and said antibodies bind to an HCV antigen, forming an antigen-antibody complex; and
    (b) reagents for detecting said antigen-antibody complex.

11. A diagnostic kit for detecting HCV E1-specific antigens in a biological sample, said kit comprising:
    (a) the fragments of claim 4, wherein said fragments are labelled and said fragments bind to an HCV antigen, forming an antigen-fragment complex; and
    (b) reagents for detecting said antigen-fragment complex.

12. An in vitro diagnostic method for detecting HCV E1-specific antibodies in a biological sample, said process comprising contacting the biological sample with an antigen, wherein the antigen contains an epitope corresponding to the peptide sequence of claims 1, 2, or 3.

* * * * *

UNITED STATES PATENT AND TRADEMARK OFFICE
CERTIFICATE OF CORRECTION

PATENT NO.   : 5,919,454
DATED        : July 6, 1999
INVENTOR(S)  : Christian Brechot et al.

It is certified that error appears in the above-identified patent and that said Letters Patent is hereby corrected as shown below:

<u>Title page,</u>
The following item should be inserted:
-- [30] Foreign Application Priority Data
    Jun. 6, 1991    [FR]    France..............................91 06882 --
Item [62] amend as follows:
-- [62]  Division of application No. 07/965,285, Mar. 18, 1993, filed as application
    No. PCT/FR92/00501 on Jun. 4, 1992, now Pat. No. 5,879,904. --

Signed and Sealed this

Fifteenth Day of July, 2003

JAMES E. ROGAN
*Director of the United States Patent and Trademark Office*